(12) United States Patent
Menon

(10) Patent No.: US 11,666,571 B2
(45) Date of Patent: Jun. 6, 2023

(54) HOST DEFENSE PROTEIN (HDP) MIMETICS FOR PROPHYLAXIS AND/OR TREATMENT OF INFLAMMATORY DISEASES OF THE GASTROINTESTINAL TRACT

(71) Applicant: INNOVATION PHARMACEUTICALS INC., Beverly, MA (US)

(72) Inventor: Krishna Menon, Beverly, MA (US)

(73) Assignee: INNOVATION PHARMACEUTICALS INC., Beverly, MA (US)

( * ) Notice: Subject to any disclaimer, the term of this patent is extended or adjusted under 35 U.S.C. 154(b) by 135 days.

(21) Appl. No.: 16/991,812

(22) Filed: Aug. 12, 2020

(65) Prior Publication Data

US 2020/0368232 A1 Nov. 26, 2020

Related U.S. Application Data

(63) Continuation of application No. 15/042,923, filed on Feb. 12, 2016, now abandoned.

(60) Provisional application No. 62/118,950, filed on Feb. 20, 2015.

(51) Int. Cl.
*A61K 31/167* (2006.01)
*A61K 31/506* (2006.01)
*A61K 45/06* (2006.01)

(52) U.S. Cl.
CPC .......... *A61K 31/506* (2013.01); *A61K 31/167* (2013.01); *A61K 45/06* (2013.01)

(58) Field of Classification Search
None
See application file for complete search history.

(56) References Cited

U.S. PATENT DOCUMENTS

2005/0031582 A1* 2/2005 Toback ................. C07K 16/18
435/325
2012/0295922 A1* 11/2012 Scott ........................ A61P 1/04
514/370

OTHER PUBLICATIONS

Richard W. Scott (Chemical Mimetics of Host Defense Proteins, PolyMedix, http://files.shareholder.com/downloads/ABEA-4ITCYZ/0x0x598955/c3e5a236-e44a-4e85-80c8-25fe7733ec65/host_defense_antimicrobial_peptides.pdf, Sep. 2012.*
Otte et al. (Polymers, 3:2010-2017, 2011).*

* cited by examiner

*Primary Examiner* — Bong-Sook Baek
(74) *Attorney, Agent, or Firm* — Ladas & Parry LLP

(57) ABSTRACT

The present invention provides methods for treating and/or preventing inflammatory diseases of the gastrointestinal tract with one or more compounds, or pharmaceutically acceptable salts thereof, disclosed herein, and the use of compositions comprising the same.

9 Claims, 15 Drawing Sheets

HOST DEFENSE PROTEIN (HDP) MIMETICS FOR PROPHYLAXIS AND/OR TREATMENT OF INFLAMMATORY DISEASES OF THE GASTROINTESTINAL TRACT

CROSS REFERENCE APPLICATION

This application is, a continuation of U.S. Ser. No. 15/042.973 filed Feb. 12, 2016, which claims the benefit of U.S. Provisional Application 62/118,950 filed Feb. 20, 2015, and incorporates the same by reference.

The present invention relates to the use of host defense protein (HDP) mimetics, including brilacidin (PMX-30063) and delparantag (PMX-60056), and the pharmaceutically acceptable salts thereof, and pharmaceutical compositions thereof in preventing and treating inflammatory diseases of the gastrointestinal tract.

BACKGROUND OF THE INVENTION

Inflammatory diseases of the gastrointestinal tract involves chronic inflammation of all or part of the digestive tract. Inflammatory diseases of the gastrointestinal tract is not a single disorder. It is the term for a group of disorders that cause prolonged inflammation of the digestive tract. Such a condition can be chronic, sub-chronic or acute and can be mild, moderate or severe according to the condition. Many diseases are included in this umbrella term. The inflammation of the digestive tract iii. all parts of the digestive tract, irrespective of the anatomical area is included in this treatment. The main symptom of active disease is usually constant diarrhea mixed with blood, of gradual onset.

The digestive tract is composed of the mouth, esophagus, stomach, small intestine, large intestine, colon, rectum, and anus. It is responsible for breaking down food, extracting the nutrients, and removing any unusable material and waste products. Inflammation anywhere along the digestive tract is included in this treatment process. The treatment includes all these conditions:

Ulcerative colitis (UC) is an inflammatory bowel disease (IBD) that causes long-lasting inflammation and sores (ulcers) in the innermost lining of the large intestine (colon) and rectum. The predominant symptom is diarrhea, associated with blood in the stool, occasionally with fever and abdominal pain. The onset may be insidious or acute (mild—60% moderate to severe—25%, fulminant-15%). A severe attack may be accompanied by dilation of the colon, known as toxic megacolon, which is associated with significant morbidity and mortality. The complications of ulcerative colitis are massive hemorrhage, stricture formation, fulminant colitis (toxic megacolon) and colon cancer. Ulcerative colitis begins in the rectum and may proceed proximally to involve either a segment of colon or the entire colon; 60% to 75% of ulcerative colitis patients have no disease proximal to the sigmoid. Pancolitis occurs in 20% of patients. Ulcerative colitis has an incidence of 1 to 20 cases per 100,000 individuals per year, and a prevalence of 8 to 246 per 100,000 individuals. Ulcerative colitis is classified according to the location of inflammation and severity of symptoms:

Ulcerative proctitis—Inflammation is confined to the area closest to the anus (rectum), and rectal bleeding may be the only sign of the disease. This form of ulcerative colitis tends to be the mildest.

Ulcerative proctosigmoiditis—Inflammation involves the rectum and sigmoid colon (lower end of the colon). Signs and symptoms include bloody diarrhea, abdominal cramps and pain, and an inability to move the bowels in spite of the urge to do so (tenesmus).

Left-sided colitis—Inflammation extends from the rectum up through the sigmoid and descending colon. Signs and symptoms include bloody diarrhea abdominal cramping and pain on the left side, and unintended weight loss.

Pancolitis—Pancolitis often affects the entire colon and causes bouts of bloody diarrhea that may be severe, abdominal cramps and pain, fatigue, and significant weight loss.

Acute severe ulcerative colitis—Previously called fulminant colitis, this rare form of colitis affects the entire colon and causes severe pain, profuse diarrhea, bleeding, fever and inability to eat.

Collagenous colitis and lymphocytic colitis also are considered inflammatory bowel diseases but are usually regarded separately from classic inflammatory bowel disease.

Crohn's disease is also an inflammatory bowel disease that causes inflammation of the lining of the digestive tract. In Crohn's disease, inflammation often spreads deep into affected tissues. The inflammation can involve different areas of the digestive tract—the large intestine, small intestine or both. Three major patterns of disease distribution are ileocecal (40%), small intestine (30%) and colon (25%). It is much less common to have involvement of the esophagus, stomach and duodenum, The most common symptoms are diarrhea, abdominal pain and weight loss. The disease is often present for months or years prior to diagnosis. In children, growth retardation may be one of major sign of indication of disease. The presence of fistula, abscess and fissures, which are commonly called as perianal disease is a distinguishing factor from ulcerative colitis, Crohn's disease is also a remitting and relapsing disease like ulcerative colitis: more than 60% of patients will require surgery within 10 years, 70% of patients will have endoscopic recurrence within one year of surgery', and 50% of patients will have symptomatic recurrence within 4 years. In Crohn's disease, the inflammation is more commonly focal, which leads to bowel wall thickening, becoming edematous and fibrotic, and the mesentery may become infiltrated with fat. The major complications of are stenosis, extensive ideal disease, extensive mucosal damage, fistulae, urinary calcium oxalate stones and carcinoma, while massive hemorrhage is less common. Crohn's disease may involve inflammation in different parts of the digestive tract in different people. The most common areas affected are the last part of the small intestine (ileum) and the colon. Inflammation may be confined to the bowel wall, which can lead to narrowing from inflammation or scarfing or both (fibrostenosis), or may funnel through the bowel wall (fistula). Narrowing may lead to a blockage (obstruction). Obstructions, stenosis and fistulas are not associated with ulcerative colitis.

Irritable bowel syndrome (IBS) is another disease that affects the digestive tract characterized by chronic abdominal pain, bloating, and diarrhea or constipation. IBS has no known specific cause, but can occur after an infection or stress. There is no cure, but treatments include dietary changes, medication, acupuncture, psychotherapy, and herbal remedies such as peppermint oil. Medications include antidepressants such as clozapine or olanzapine, laxatives, antidiarrheal serotonin antagonists (5HT3), such as ondansetron, clozapine or ondansetron, or serotonin reuptake inhibitors (SSRIs), anti-spasmodics, such as hyoscyamine or dicyclomine, proton pump inhibitors (PPIs), magnesium aluminum silicates, alverine citrate drugs and rifaximin. IBS affects about 15% of the US population.

Inflammatory Bowel Disease

The exact causes of IBD are not yet fully understood. Accumulating evidence suggests that the immune response has long been involved in pathogenesis of MD.

The intestinal microbiome consists of the microorganisms that inhabit the gut. Host-microbiome interactions can be mutually beneficial or can be deleterious, inciting intestinal inflammation. The intestinal epithelium at the interface between the intestinal microbiome and the lymphoid tissue associated with the gastrointestinal system plays a critical role in shaping the mucosal immune response. Intestinal epithelial cells are a physical barrier against excessive entry of bacteria and other antigens from the intestinal lumen into the circulation. Additional defenses against bacterial invasion consist of specialized epithelial cells, including goblet cells and Paneth cells. Goblet cells regulate the production of mucus and factors that contribute to epithelial repair and regulation of inflammation. Paneth cells secrete antimicrobial peptides such as α-defensins. Intestinal mucus overlies the epithelium, thereby limiting contact between bacteria and epithelial cells. In inflammatory bowel disease, however, the inflammatory response often results in continued epithelial injury, which causes erosion, ulcerations, and decrease in the production of defensin. The result is increased exposure to intestinal microbiota and amplification of inflammatory response.

The intestinal lamina propria contains a complex population of immune cells that balance the requirement for immune tolerance of luminal microbiota with the need to defend against the pathogen, excessive entry of luminal microbiota, or both. The hallmark of active inflammatory bowel disease is a pronounced infiltration into the lamina propria of innate immune cells (neutrophils, macrophages, dendritic cells, and natural killer T cells) and adaptive immune cells (T cells and B cells). Increased numbers and activation of these cells in the intestinal mucosa elevate local levels of TNF-α, interleukin-1β, interleukin-6 (IL-6), interferon-gamma (IFN-γ), and cytokines of the interleukin-23-Th17 pathway.

The proinflammatory cytokine TNF-alpha has been identified as playing a pivotal role in the inflammatory cascade that causes chronic inflammation, as observed in IBD. Levels of circulating IL-6 are elevated in several inflammatory diseases including Crohn's disease. IL-6 is key modulator of inflammatory response. Influencing the production of this cytokine can change the balance of effector CD4+ T cell subsets and induce B cell antibody production. Moreover, given that IL-6 is mostly produced from innate cells such as macrophages, neutrophils and mast cells, it is a strategic bridge between the innate and the adaptive system.

There are no curative therapeutic treatments for IBD. The only cure for UC is surgical removal of the large intestine, which reduces quality of life. To allay symptoms, dietary and lifestyle changes are important. Anti-inflammatory steroids are commonly used but they can also induce severe side effects. One anti-inflammatory used for IBD is mesalazine (also known mesalamine or 5-aminosalicyclic acid), but it is more effective in UC than in Crohn's disease. Immunomodulators such as azathioprine, methotrexate, infliximab, adalimumab, certolizumab and natalizumab are also used for Crohn's disease. Long term use of antibiotics is somewhat effective for Crohn's disease, but is not effective in UC. Chronic use of antibiotics carries the risk of developing drug-resistant microbes. Some individuals resort to probiotics, fish oil, acupuncture, or homeopathic treatments to try to alleviate symptoms. In addition to the effects on the digestive system, IBD can also lead to nutrient deficiency, iritis, uveitis, skin rashes, arthritis, primary sclerosing cholangitis anklosing spondylitis, pyoderma gangrenosum, and erythema nodosum. Inflammatory bowel disease affects approximately 1.4 million Americans, and its peak onset is in persons 15 to 30 years of age.

Development of Host Defense Protein Mimetic for Inflammatory Diseases

Host defense peptides were originally studied for their direct antimicrobial activities and have also been found to exhibit multifaceted immunomodulatory activities. Despite the large diversity observed in HDPs, they generally adopt highly conserved amphipathic topologies in which the hydrophilic and hydrophobic side chains segregate into distinctly opposing regions or faces of the molecule. An example of a molecule with amphipathic structure is magainin 2. Magainins were first discovered in the African clawed frog [Zasloff M. Magainins, a class of antimicrobial peptides from *Xenopus* skin; isolation, characterization of two active forms, and partial cDNA sequence of a precursor. *PNAS* 8415449-5453 (1987)].

Biological macromolecules, including proteins and RNA, generally adapt unique folded conformations that are responsible for their remarkable properties. Until recently, the process of folding was considered a mystery, but as the fields of protein folding, RNA structure and molecular organization have evolved, it has become increasing possible to design non-biological molecules that fold into unique structures. To mimic natural proteins, investigators have synthesized oligomers by sequentially coupling individual monomer units to provide homogeneous linear molecule of entirely uniform sequence and chain length. Oligomers that fold into well-defined secondary structure have come to be foldamers (Hill D J, et al., *Chem. Rev.* 2001, 101, 38934012; Horne W S, et al., *Acc. Chem. Res.* 2008, 41, 1399-1408; Patch J A. Barron A E, *J Am. Chem. Soc.* 2003, 125, 12092-12093). The structural simplicity and relative ease of synthesis of many foldamers allows them to be used as three-dimensional scaffolds for molecular recognition.

An example of the design, synthesis, and antimicrobial activity of arylamide polymers and oligomers is presented in Tew et al. (Tew et al., *Proc. Natl. Acad. Sci. USA,* 2002, 99, 5110-5114), which is incorporated herein by reference in its entirety. These compounds, including brilacidin (PMX-30063) and delparantag (PMX-60056), were synthesized to mimic naturally occurring antimicrobial peptides. Both PMX-30063 and PMX-60056 have similar spatio-topology which mimic the HDP structure in space.

Numerous studies with linear and cyclic peptides have strongly supported the hypothesis that their physicochemical properties, rather than any precise sequence, are responsible for their ability to selectively disrupt membranes. Therefore, a series of non-peptidic analogues of the HDPs (HDP mimetics) has been developed and evaluated for their potential antibacterial activity. Optimization of both total charge and the hydrophobic content proved to be particularly important to the design of compounds that are highly active and nontoxic in animals. Host defense proteins (HDP) are key components of innate immune systems and play dual roles: rapid microbial killing and subsequent immune modulation. PMX-30063 [$N^4$, $N^6$-bis(2-((R)-pyrrdlidin-3-yloxy)-3-((4-carbamoylbutyl) guanidine)-5-(trifluoromethyl)phenyl)pyrimidine-4,6-dicarboxamide tetrahydrochloride salt, molecular formula: $C_{40}H_{50}F_6N_{14}O_6 \cdot 4$ HCL, USAN name: brilacidin] and PMX-60056 [Tetra-[(L)-lysyl-5-amino-o-methylsalicylamide, molecular formula: $C_{56}Hg_{84}Cl_5N_{13}O_{12} \cdot 5$ HCl] are non-peptide mimics of HDP that have distinct advantages over proteins for pharmaceutical uses. These HDP mimetics demonstrated rapid bactericidal activity as well as anti-inflammatory and immunomodulatory effects (Som A, Navasa N, Percher A, Scott R W, Tew G N, Anguita. Identification of Synthetic Host Defense Peptide Mimics That Exert Dual Antimicrobial and Anti-Inflammatory Activities, *Clin and Vaccine Immunol.* 2012, 19:1784-1791; Scorciapino M A Rinaldi A C. Antimicrobial peptidomimetics: reinterpreting nature to deliver innovative therapeutics. Patricia Méndez-Samperio. *Front. Immunol* 2012, Vol 3, Article 171; Peptidomimetics as a new generation of antimicrobial agents: current progress. *Infection and Drug Resistance* 2014:, 7229-237), A wide range of immunomodulatory functions have been defined for HDP that result in net suppression of potentially harmful proinflammatory response (Hilchie A L, et al., *Nat. Chem. Biol.*, 2013, 9, 761-768). Their diverse immunomodulatory capability includes the modulation of pro-and anti-inflammatory response (Mansour S C, et cd., *Trends in Immunology* 2014, 35, 443-450) and acting as immunomodulators in both innate and adaptive immune response (Wong J H, et al *Curr Protein Pept Sci* 2013, 14, 504-514). Although the anti-inflammatory function of HDP was known, the molecular mechanism of action of HDP was poorly understood. The present inventors hypothesized that HDP may be functioning through the cyclic AMP/cyclic GMP pathways in suppression of proinflammatory response. The present inventors tested this hypothesis and found that the Host Defense Protein (HDP) mimetics PMX-30063 and PMX-60056 inhibit phosphodiesterase (PDE) in vitro, as detailed herein. Phosphodiesterase is a family of enzymes that catalyze the breakdown of signaling molecule cyclic AMP/or cyclic GMP. cAMP and cGMP are ubiquitous secondary-messenger signaling molecules produced by a large family of cyclases that participate in a multitude of signaling processes.

PDE inhibitors have shown anti-inflammatory activity in a variety of preclinical models (Martinez A, Gil C. *Expert opinion on therapeutic patents* 2014, 24, 1311-1321). PDE4 has received particular attention due to the fact that all of the inflammatory and immunomodulatory cells not only express PDE4, but also that specific functions of these cells are broadly inhibited by selective PDE4 inhibitors. PDE4 is a predominant phosphodiesterase expressed in neutrophils, T cells and macrophages. PDE4 inhibitors reduce neutrophil chemotaxis, recruitment and activation; inhibit the activation of CD4+ and CD8+ T cells; and inhibit monocytes chemotaxis (Tamimi A, et al. *Resp. Med* 2012, 106, 319-328). The discovery by the present inventors that PMX-30063 and PMX,-60056 are PDE inhibitors, discussed below, indicates that these compounds described herein are expected to be useful in the treatment of inflammatory diseases of the gastrointestinal tract and should be further investigated in a clinical study as discussed in Example 19.

SUMMARY OF THE INVENTION

Figure 1:
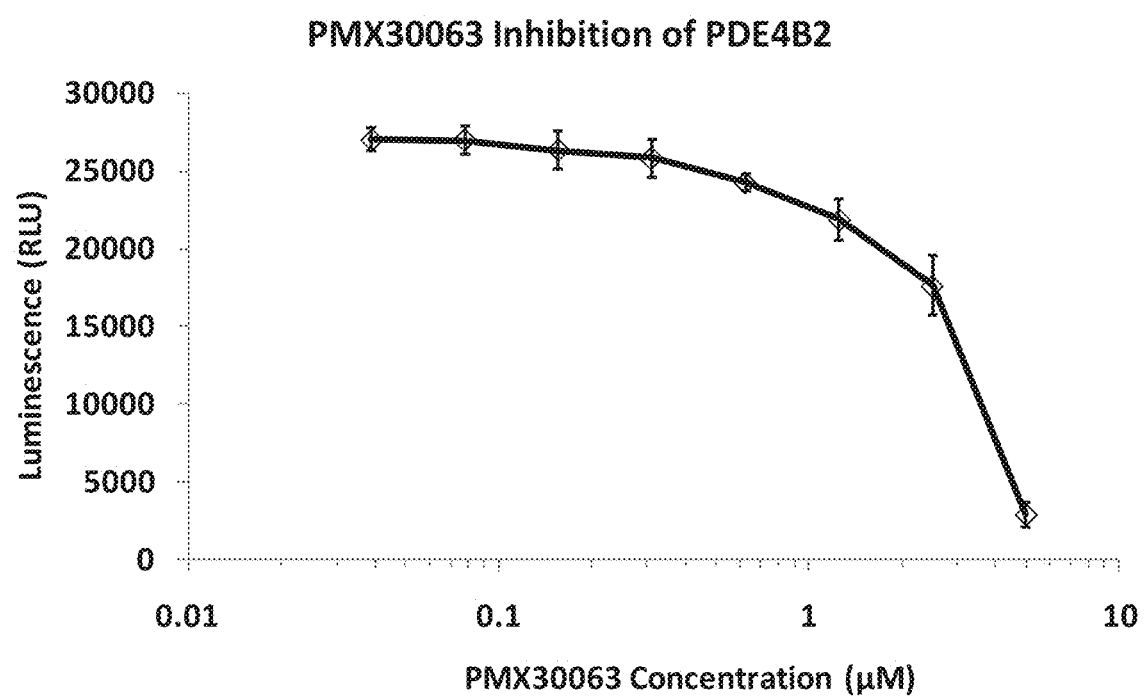
FIG. 1 illustrates that PMX-30063 inhibited PDE4 with an IC50 in the 3 µM range (n=5).

The present invention relates to methods of prophylaxis and/or treatment of inflammatory diseases of the gastrointestinal tract in a mammal comprising administering to the mammal in need of such prophylaxis and/or treatment a therapeutically elective amount of a compound selected from brilacidin (PMX-30063) and delparantag (PMX-60056) and pharmaceutically acceptable salts thereof. In one embodiment, brilacidin and delparantag are administered together. In another embodiment, the inflammatory disease is inflammatory bowel disease ulcerative colitis, collagenous colitis, lymphocytic colitis, Crohn's disease, or irritable bowel syndrome. In another embodiment, said compound is administered together with an antibiotic other than brilacidin or delparantag.

The present invention also relates to the use of pharmaceutical compositions for treatment of inflammatory diseases of the gastrointestinal tract comprising a therapeutically effective amount of a compound selected from brilacidin and delparantag and pharmaceutically acceptable salts thereof and a pharmaceutically acceptable carrier. Diseases include, but are not limited to inflammatory bowel disease ulcerative colitis, collagenous colitis, lymphocytic colitis, Crohn's disease, and irritable bowel syndrome. In one embodiment, the pharmaceutical composition comprises both brilacidin and delparantag. In another embodiment, the composition comprises brilacidin or delparantag and an antibiotic other than brilacidin. In another embodiment, the composition comprises brilacidin or delparantag and is administered together with an antibiotic other than brilacidin.

The present invention also provides active compounds, or pharmaceutical comprising the same, for use in the preparation of a medicament for prophylaxis and/or treatment of inflammatory diseases of the gastrointestinal tract in a patient. In one embodiment, the pharmaceutical composition comprises both brilacidin and delparantag. In another embodiment, the composition comprises an antibiotic other than brilacidin.

The structural formulae of brilacidin and delparantag are shown below.

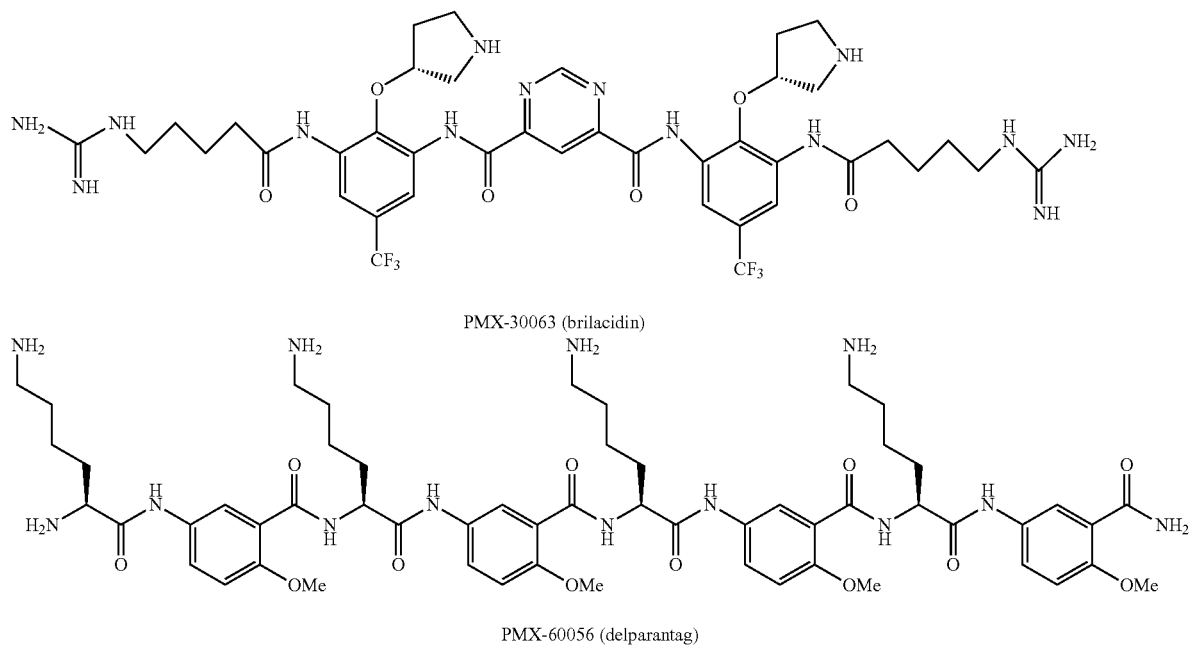

PMX-30063 (brilacidin)

PMX-60056 (delparantag)

The present invention also provides pharmaceutical compositions for prophylaxis and treatment of inflammatory diseases of the gastrointestinal tract in a mammal comprising an effective amount of one or more of the compounds described above, or one or more salts thereof, and a pharmaceutically acceptable carrier. Suitable compositions include, but are not limited to, oral non-absorbed compositions. Suitable compositions also include, hut are not limited to saline, water, cyclodextrin solutions, and buffered solutions of pH 3-9.

DETAILED DESCRIPTION OF THE INVENTION

The starting materials, which are required to prepare the compound brilacidin and the pharmaceutically acceptable salts thereof are commercially available in bulk. The compound brilacidin and the salts are prepared by a) reacting (R)-(-)-N-Boc-3-pyrrolidinol with 2-chloro-5-(trifluoromethyl)-1,3-dinitrobenzene in the presence of potassium ter-butoxide to form a compound having Formula I b) reacting the compound of Formula I with an alcohol and a transition metal catalyst in the presence of hydrogen to form a compound of Formula II

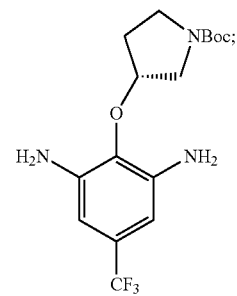

c) adding the compound of Formula II and pyrimidine-4,6-dicarboxylic acid in the presence of N-(3-dimethylaminopropyl)-N'-ethylcarbodiimide hydrochloride in pyridine to form a compound of Formula III

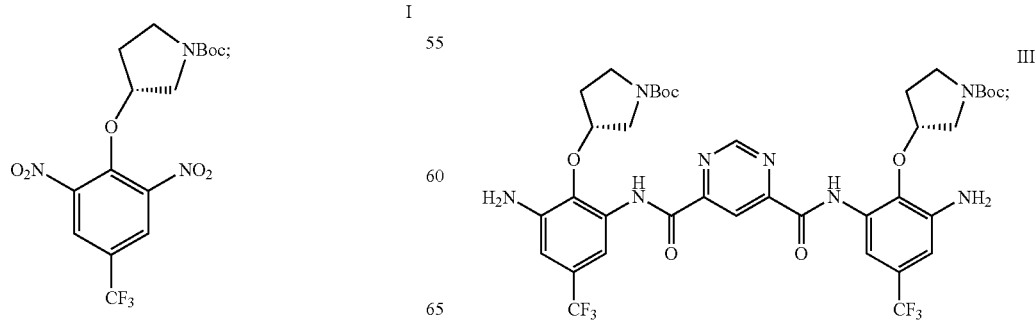

d) reacting the compound of Formula III with 5-(carbobenzoxyamino)valeric acid to form a compound of Formula IV

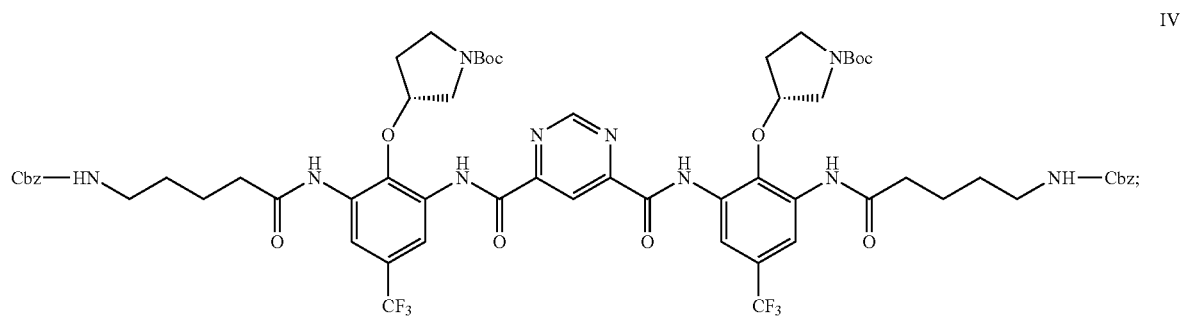 [SMILES: CC(C)(C)OC(=O)N1CC[C@@H](Oc2c(NC(=O)CCCCNC(=O)OCc3ccccc3)cc(C(F)(F)F)cc2NC(=O)c2cc(C(=O)Nc3cc(C(F)(F)F)cc(NC(=O)CCCCNC(=O)OCc4ccccc4)c3O[C@@H]3CCN(C(=O)OC(C)(C)C)C3)ncn2)C1]

e) reducing the resultant compound of formula IV in the presence of an alcohol, a transition metal catalyst, and hydrogen to afford formula V

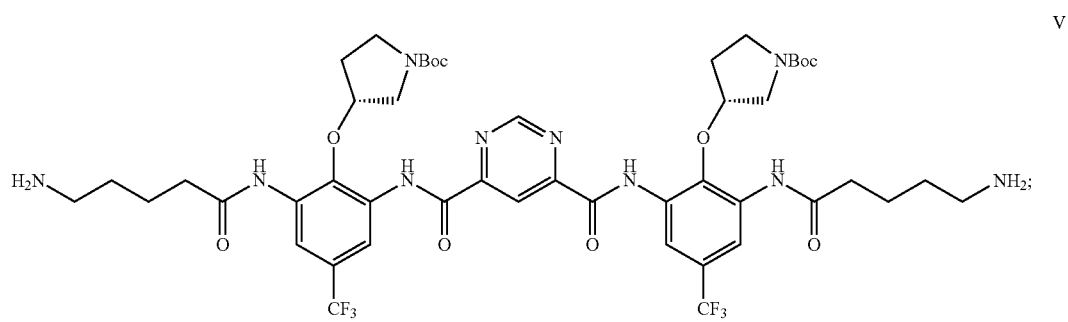 [SMILES: CC(C)(C)OC(=O)N1CC[C@@H](Oc2c(NC(=O)CCCCN)cc(C(F)(F)F)cc2NC(=O)c2cc(C(=O)Nc3cc(C(F)(F)F)cc(NC(=O)CCCCN)c3O[C@@H]3CCN(C(=O)OC(C)(C)C)C3)ncn2)C1]

f) reacting the resultant compound of V with di-N-Boc pyrazole in the presence of base to provide compound of formula VI ;

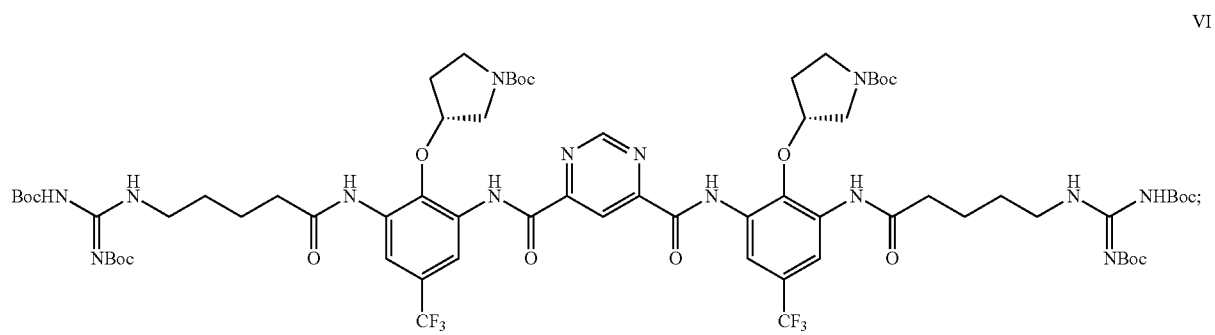

and deprotecting, the compound of Formula VI using acid to produce PMX-30063 (brilacidin); and, if desired, preparing a pharmaceutically acceptable salt.

The compound delparantag and the pharmaceutically acceptable salts thereof, are prepared by (a) removing the Cbz groups from a compound of Formula VII

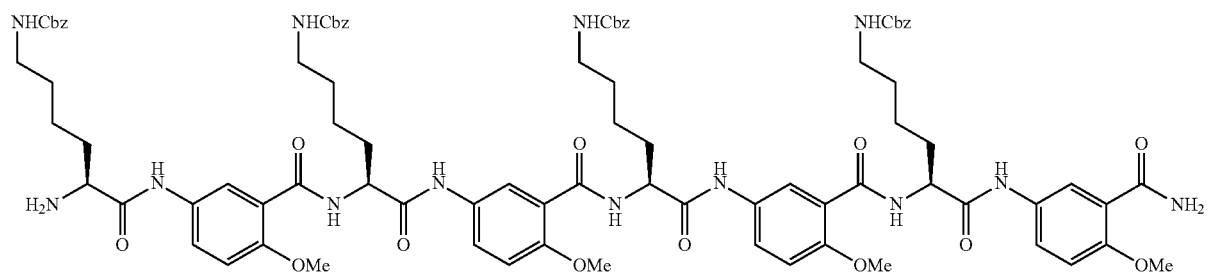

VII or a pharmaceutically acceptable salt thereof, using hydrogen gas and transitional metal catalyst to form the delparantag, or pharmaceutically acceptable salt thereof, and (b) optionally isolating the delparantag or pharmaceutically acceptable salt thereof and if desired preparing a pharmaceutically acceptable salt from the compound delparantag.

Examples of suitable hydrogenation/hydrogenolysis conditions that can be used in step a) include those conditions known in the art of synthetic organic chemistry. For example, $H_2$ gas and a transitional metal catalysts such as Pd-C (5-10%), Pd(OH)$_2$, Platinum metal and Raney-Nickel can be used The reaction can be carried out at a suitable temperature, for example, ambient temperature (about 20-25° C.) or up to a temperature at which the solvent in the reaction mixture is at reflux.

PMX-60056, or a pharmaceutically acceptable salt thereof, can be isolated (including purification) by various techniques known in the art. For example, in some cases it might be desired to isolate the reaction product by filtration and subsequent precipitation of the product from the filtrate or crystallization For another example, in some cases it might be desired to isolate the reaction product by extraction with an appropriate solvent or mixture of solvents, for example diethyl ether or ethyl acetate, and subsequent chromatography on silica gel such as 3-mercaptopropyl ethylsufided silica gel or by trituration with an appropriate solvent such as methylene chloride, methanol or a mixture of solvents. The recrystallization can be performed with a solvent, or with a mixture of solvents. In some embodiments, isolation of product includes removal of transitional metal catalyst from the reaction product and levels of metal catalyst can be determined by a suitable method such as Inductively Coupled Plasma (ICP). The purity of the isolated (or purified) product can be determined by a suitable method such as using HPLC.

The starting materials; methyl 5-amino-2-methoxybenzoate and Boc-Lys(Cbz)-OH are commercially available, and can be easily obtained from commercial suppliers for the preparation of compound formula VII.

In some embodiments, the compound of Formula VII, or pharmaceutically acceptable salt thereof, used in step a) can be prepared by:

c) removing the Boc group to from a compound of Formula VIII:

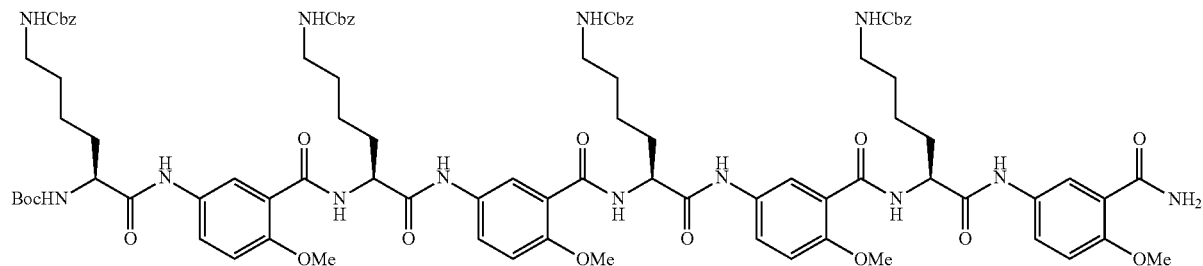

VIII or pharmaceutically acceptable salt thereof, to form the compound of Formula VII or pharmaceutically acceptable salt thereof.

Removal of the Boc group can be carried out by using a suitable reagent such as an acid (e.g., $H_3PO_4$, TFA, HCl, TsOH, or $H_2SO_4$) or TMSOTf/2,6-lutidine or a solution of reagent, in a suitable polar or halogenated solvent such as THF, EtOAc, dioxane, dioxane, water, or $CH_2Cl_2$ or a mixture of any two or more of these solvents at a suitable temperature for example, ambient temperature (about 20-25° C.). The reaction product of step c) can be isolated as either a salt of the compound of Formula VII or free base, neutralizing with NaOH as a base to neutralize the acid salt.

In some embodiments, the compound of Formula VIII, or pharmaceutically acceptable salt thereof, used in step c) can be prepared by:

d) reacting a compound of Formula IX:

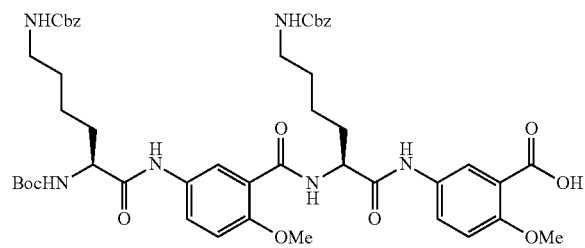

or a pharmaceutically acceptable salt thereof with a compound of Formula X:

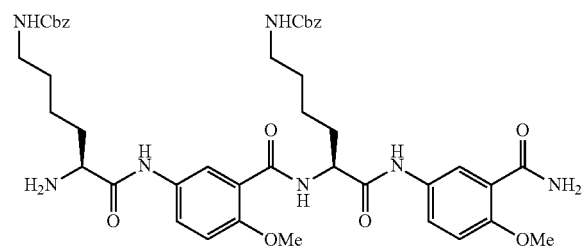

or pharmaceutically acceptable salt thereof.

The reaction of step d) can be carried out in the presence of a coupling reagents such as dimethylamino)phosphonium hexafluorophosphate (BOP), 2-(1H-benzotriazol-1-yl)-1,1,3,3-tetramethylumnium hexafluorophosphate (HBTU), O-(7-azabenzotriazol1-yl)-N,N,N', N'-tetra hexafluorophosphate (HATU), 1-ethyl-3-3-dimethylaminopropyl)carbodiimide, dicyclohexylcarbodimide (DCC), N,N'-diisopropykarbodiimide (DIC), benzotriazol-1-yl-oxytripyrrolidinophosphonium hexafluorophosphate (Py-BOP) N,N'-carbonyldiimidazole (CDI), N-hydroxybenzotriazole (HOBt), 1H-Benzotriazolium 1-[(bis(dimethyl-amino)methylenel]-5-chlorohexafluorophosphate (1-),3-oxide (HCTU), a suitable 1,3,5-triazine derivative (see, for example, Kaminski, Tetrahedron Letters, 1985, 26, 2901-2904; examples of suitable 1,3,5-triazine derivatives include, but are not limited to, 2,4,6-tichloro-1,3,5-triazine, 2-chloro-4,6-diphenoxy-1,3,5-triazine; 2-chloro4,6-dibenzyloxy-1,3,5-triazine; 2-chloro-4,6-dimethoxy-1,3,5-triazine; 2,4-dichloro-6-phenoxy-1,3,5-triazine, 2,4-dichloro-6-benzyloxy-1,3,5-triazine; or 24-dichloro-6-methoxy-1,3,5-triazine), and a mixture of two or more thereof. If desired, the coupling reagent in step d) includes a mixture of EDAC and HOBt and an organic base, to form the compound of Formula VIII, or pharmaceutically acceptable salt thereof.

The coupling reagent in step d) is chosen from those that prevent racemization of any chiral center present in the reactants (and/or reaction products) (see, Konig et aL., Chem, Ber., 1970, 103, 788; listing HOBt as such a coupling reagent). The coupling reaction can be carried out in the presence of a suitable base. Examples of suitable bases include, but are not limited to, triethylamine (TEA), diisopropylethylamine N-methylmorpholine (NMM), N-N-dimethylaminopyridine (DMAP), pyridine, and imidazole.

The reaction in step d) can be carried out in a suitable solvent such as a polar solvent, for example, an ether, (e.g., tetrahydrofuran (THF), a halogenated solvent (such as dichloromethane (DCM) or chloroform), or a mixture of suitable solvents at a suitable temperature, for example, ambient temperature (20-25° C.)) or up to a temperature at which the solvent in the reaction mixture is at reflux. The reaction product of step d) can be isolated (including purification) by any suitable techniques known in the art.

The compound of Formula X, oar pharmaceutically acceptable salt thereof, used in step d) can be prepared by:

e) reacting a compound of Formula IX:

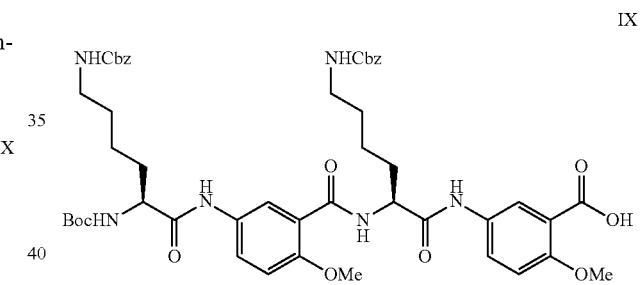

or, pharmaceutically acceptable salt thereof, with ammonia or an ammonia producing reagent, to form a compound of Formula XI:

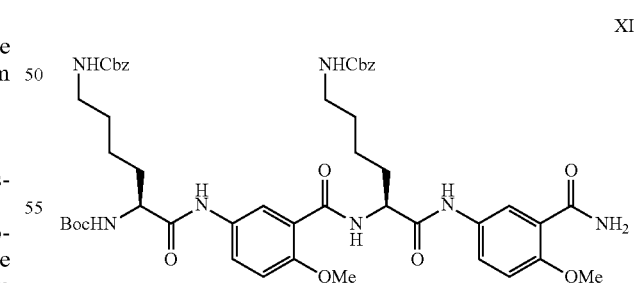

or pharmaceutically acceptable salt thereof; and f) removing the Boc group from the compound of Formula XI, or pharmaceutically acceptable salt thereof, to form the compound of Formula X, or pharmaceutically acceptable salt thereof.

The coupling reaction of step e) is carried out in the presence of a coupling reagent and an organic base. Suitable coupling reagents and organic bases are known in the art.

Ammonia (either neat or in a solvent such as water or dioxane) may be used in step e). An ammonia producing reagent (such as NH₄Cl) may be used.

Removal of the Boc group in step f) can be carried out by using a suitable acid reagent (e.g., H₃PO₄, TFA, HCl, TsOH, or H₂SO₄) or a solution of reagent in a solvent (HCl-dioxane, HCl-ethyl acetate.

The compound of Formula VIII, or pharmaceutically acceptable salt thereof, used in the present invention can be prepared by:

g) hydrolyzing a compound of Formula XII:

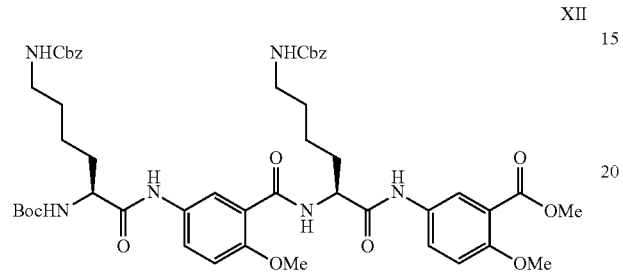

XII or pharmaceutically acceptable salt thereof, in the presence of a suitable base such as (e.g., LiOH, NaOH, KOH, Ba(OH)₂) and metal carbonate (e.g., Na₂CO₃, K₂CO₃, and Cs₂CO₃), to form the compound of Formula IX.

The compound of Formula XII, or pharmaceutically acceptable salt thereof, used in the present invention can be prepared by:

h) reacting a compound of Formula XIII:

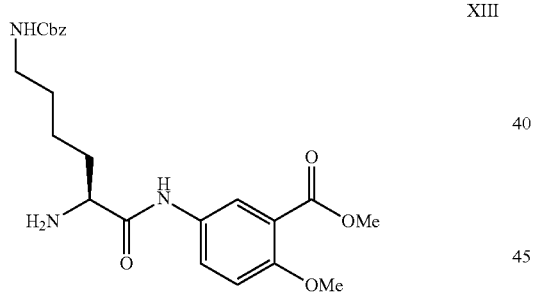

XIII or pharmaceutically acceptable salt thereof, with a compound of Formula XIV:

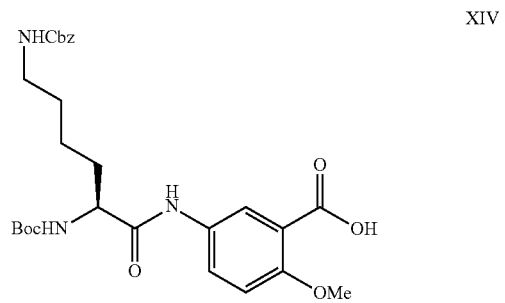

XIV or pharmaceutically acceptable salt thereof, to form the compound of Formula XII, or pharmaceutically acceptable salt thereof.

The coupling reaction of step h) may be carried out in the presence of a coupling reagent and an organic base, where suitable coupling reagents and organic bases are known in the art. In some embodiments, the coupling reaction of step h) is carried out in the presence of a coupling reagent. In some embodiments, the coupling reagent in step h) includes a mixture of EDAC and HOBt.

In some embodiments, the organic base in step h) is NMM.

The compound of Formula XIII or pharmaceutically acceptable salt thereof, used in the present invention can be prepared by:

i) hydrolyzing a compound of Formula XV:

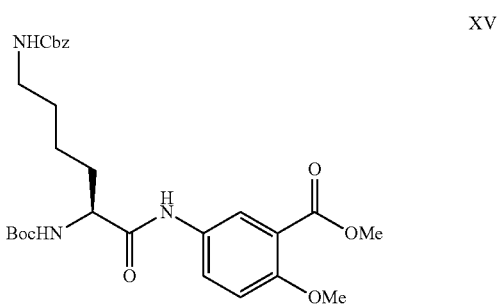

XV or pharmaceutically acceptable salt thereof; in the presence of a base, to form a compound of Formula XIV:

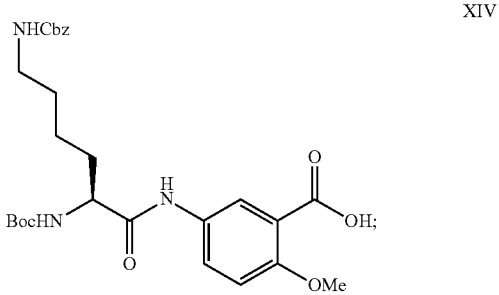 [SMILES: COc1ccc(NC(=O)[C@H](CCCCNC(=O)OCc2ccccc2)NC(=O)OC(C)(C)C)cc1C(=O)O]

XIV and j) removing the Boc group from a compound of Formula XIV, or pharmaceutically acceptable salt thereof, to form the compound of Formula XV, or pharmaceutically acceptable salt thereof. Removal of the Boc group can be carried out by using a suitable reagent or suitable reagents, such as an acid (e.g., H₃PO₄, TFA, HCl, TsOH, or H₂SO₄) or TMSOTf/2,6-lutidine. An acid (e.g., TsOH) is used for removal of the Boc Group.

Examples of suitable hydrolyzing bases in step i) include, but are not limited to, metal hydroxide (e.g., LiOH, NaOH, KOH, Ba(OH)₂) and metal carbonate (e.g., Na₂CO₃, K₂CO₃, and Cs₂CO₃). In some embodiments, the base in step i) is LiOH.

In some embodiments, the compound of Formula XV, or pharmaceutically acceptable salt thereof, used in the present invention can be prepared by:

k) reacting a compound of Formula XVI:

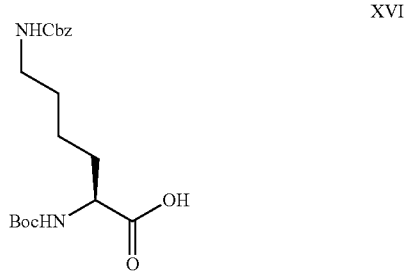 [SMILES: CC(C)(C)OC(=O)N[C@@H](CCCCNC(=O)OCc1ccccc1)C(=O)O]

or pharmaceutically acceptable salt thereof, with a compound of Formula XVII:

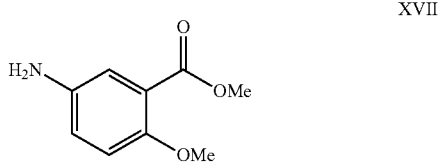 [SMILES: COC(=O)c1cc(N)ccc1OC]

or pharmaceutically acceptable salt thereof, to form the compound of Formula XV, or pharmaceutically acceptable salt thereof.

In some embodiments, the coupling reaction of step k) is carried out in the presence of a coupling reagent and an organic base. Suitable coupling reagents and organic bases are known in the art. In some embodiments, the coupling reaction of step k) is carried out in the presence of a coupling reagent. In some embodiments, the coupling reagent in step k is a mixture of EDAC and HOBt. In some embodiments, the or base in step k) is NMM.

Compounds of the invention can be synthesized by solid-phase>synthetic procedures well known to those of skill in the art (see, Tew et al,, *Proc. Natl. Acad. Sci. USA,* 2002, 99, 5110-5114; Barany et al., *Int. J. Pept. Prot. Res.,* 1987, 30, 705-739: Solid-phase Synthesis: A Practical Guide, Kates, S. A., and Albericio F., eds., Marcel Dekker, New York (2000), and Dörwald, F. Z., Organic Synthesis on Solid Phase: Supports, Linkers, Reactions, 2nd Ed., Wiley-VCR, Weinheim (2002)).

As used herein, the term "about" means ±5% of the value it describes. For example, about 100 means from 95 to 105.

As used herein, "isolated" means that compounds are separated from other components of a synthetic organic chemical reaction mixture, such as by conventional techniques, and are purified.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "purified" means that, when isolated, the isolate contains at least 90%, at least 95%, at least 98%, or at least 99% of the desired compound I by weight of the isolate.

As used herein, the phrase "pharmaceutically acceptable salt(s)" includes, but is not limited to, salts of acidic or basic groups. Suitable examples of salts include, for example, hydrochloric acid and triflouroacetic acid salts.

In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, or excipient with which a compound selected from PMX-30063 and PMX-60056 and the pharmaceutically acceptable salts thereof (hereinafter also referred to as active compounds) is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used. When administered to a human, the active compounds and pharmaceutically acceptable carriers can be sterile. Water is a suitable carrier when the compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, suppository, aerosol, spray, or any other form suitable for use. Examples of suitable pharmaceutical carriers are described in Remington's Pharmaceutical Sciences, A. R. Gennaro (Editor) Mack Publishing Co.

The active compounds are formulated in accordance with routine procedures as a pharmaceutical composition adapted for administration to humans. Typically, the active compounds are administered as solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the compound of the invention is to be administered by infusion, it can be dispensed, for example, with an infusion bottle containing sterile pharmaceutical grade water or saline. Where the active compound is administered by injection, an ampoule of sterile water for injection or saline can be provided so that the ingredients may be mixed prior to administration.

The active compounds, and compositions comprising the same, can be administered orally. Compounds and compositions for oral delivery can be in the form of, for example, tablets, lozenges, aqueous or oily suspensions granules, powders, emulsions, capsules, syrups or elixirs. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation.

Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered active compounds. Oral compositions can include standard vehicles such as mannitol, lactose, starch, magnesium stearate, sodium saccharine, cellulose, magnesium carbonate, etc. Such vehicles are suitably of pharmaceutical grade.

The pharmaceutical compositions can be in unit dosage form. In such form, the composition can be divided into unit doses containing appropriate quantities of the active component. The unit dosage from can be a packaged preparation, the package containing discrete quantities of the preparations, fur example, picketed tablets, capsules, and powders in vials or ampules. The unit dosage form can also be a capsule, cachet, or tablet itself, or it can be the appropriate number of any of these packaged forms.

The following non-limiting Examples illustrate the compositions and methods disclosed herein and the preparation of the compounds disclosed herein.

Brillacidin and Delparantag in the Treatment of Inflammatory Diseases of the Gastrointestinal Tract The compounds brilacidin (PMX-30063) and delparantag (PMX-60056), and the pharmaceutically acceptable salts thereof, hereinafter also referred to as the active compounds, may be administered for the treatment of inflammatory diseases of the gastrointestinal tract in any conventional manner by any route where they are active. Administration can be systemic, rectal, or oral. For example, administration can be, but is not limited to, parenteral, subcutaneous, intravenous, intramuscular, intraperitoneal, transdermal, oral or buccal routes, or by depot injections or implants. Thus, modes of administration for these compounds (either alone or in combination with other pharmaceuticals) can be, but are not limited to, sublingual, injectable (including short-acting, depot, implant and pellet forms injected subcutaneously or intramuscularly), or by use of rectal suppositories, intrauterine devices, and transdermal forms such as patches and creams. The selection of the specific route of administration and the dose regimen is to be adjusted or titrated by the clinician according to methods known to the clinician to obtain the desired clinical response. The amount of the compounds of the invention to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). The amount of a compound described herein that will be effective in the treatment and/or prevention of inflammatory diseases of the gastrointestinal tract will depend on the nature and severity of the inflammatory disease, and can be determined by standard clinical techniques. In addition, in vitro or in vivo assays may optionally be employed to help identify optimal dosage ranges. The precise dose to be employed in the compositions will also depend on the route of administration, and the seriousness of the disorder, and should be decided according to the judgment of the practitioner and each patient's circumstances. However, a suitable dosage range for oral administration is, generally, from about 0.001 milligram to about 1000 milligrams per kilogram body weight. In some embodiments, the oral dose is from about 0.01 milligram to 100 milligrams per kilogram body weight, from about 0.01 milligram to about 70 milligrams per kilogram body weight, from about 0.1 milligram to about 50 milligrams per kilogram body weight, from 0.5 milligram to about 20 milligrams per kilogram body weight, or from about 1 milligram to about 10 milligrams per kilogram body weight. In some embodiments, the oral dose is about 5 milligrams per kilogram body weight. For oral administration, the active compounds may be administered in a tablet form containing 100 mg per tablet or in liquid form by dissolving water to a concentration of 1 to 10 mg/mL. The resulting formulation is a clear colorless solution at pH 7. The active compounds may be given by daily doses until the condition has resolved, For—rectal administration, 25 mg or 50 mg is given as a retention enema, in a 60 mL sterile solution. The enema is given either once daily at bedtime or twice daily in the morning and at bedtime for 6 weeks. If brilacidin (PMX-30063) and delparantag (PMX-60056) are administered in a single pharmaceutical composition or concurrently the total daily dose of the two compounds will generally be comparable to the amounts set forth above for the daily dose of a single compound.

The total daily dose may be administered in single or divided doses. The present invention also encompasses sustained release compositions. These dosages are based on an average human subject having a weight of about 65 kg to 70 kg. The physician will readily be able to determine doses for subjects whose weight falls outside this range, such as infants and the elderly.

The pharmaceutical compositions and/or formulations containing one or both of the active compounds and a suitable carrier can be solid dosage forms which include, but are not limited to, tablets, capsules, cachets, pellets, pills, powders and papules; topical dosage forms which include but are not limited to, solutions, powders, fluid emulsions, fluid suspensions, semi-solids, ointments, pastes, creams, gels and jellies, and foams; and parenteral dosage forms which include, but are not limited to, solutions, suspensions emulsions, and dry powder; comprising an effective amount of a compound of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance (see, for example, Modern Pharmaceutics Banker & Rhodes, Marcel Dekker, Inc. (1979); and Goodman & Gilman's The Pharmaceutical Basis of Therapeutics, 6th Edition, MacMillan Publishing Co., New York (1996)). Descriptions of pharmaceutical compositions and methods for then preparation may be found, for example, in 'Remington's Pharmaceutical Sciences', 19th Edition (Mack Publishing Company, 1995).

In some embodiments, the active compounds can be used with agents including, but not limited to, topical analgesics (e.g., lidocaine). The active compounds may also be administered together with antibiotics. Examples of such antibiotics are amoxicillin, ampicillan, azlocillin, bacitracin, carbenicillin, cefaclor, cefamandole, cefazolin, cefmetazole, cefoperazone, cefotaxime, cefsulodin, ceftriaxone, cephalexin, cephalosporin C, cephalothin, cephradine, cloxacillin, D-cycloserine, dicloxacillin, D-penicillamine, econazole, ethambutol, lysostaphin, moxalactam, nafcillin, nikkomycin Z, nitrofurantoin, oxacillin, penicillic, penicillin G, phenethicillin, phenoxymethylpenicillinic acid, phosphomycin, pipemidic acid, piperacillin, ristomycin, and vancomycin; amikacin, anisomycin, apramycin, azithromycin, blasticidine S, brefeldin A, butirosin, chloramphenicol, chlortetracycline, clindamycin, clotrimazole, cycloheximide, demeclocycline, dibekacin, dihydrostreptomycin, doxycycline, duramycin, emetine, erythromycin, fusidic acid, G 418, gentamicin, helvolic acid, hygromycin B, josamycin, kanamycin, kirromycin, lincomycin, meclocycline, mepartricin, midecamycin, minocycline, neomycin, netilmicin, nitrofurantoin, nourseothricin, oleandomycin, oxytetracycline, paromomyein, puromycin, rapamycin, ribostamycin, rifampicin, rifamycin, rosamicin, sisomicin, spectinomycin, spiramycin, streptomycin, tetracycline, thiamphenicol, thiostrepton, tobramycin, tunicamycin, tylosin, viomycin, and virginiamycin;camptothecin, 10-deacetylbaccatin III, azacytidine, 7-aminoactinomycin D, 8-quinolinol, 9-dihydro-13-acetylbaccatin III, aclarubicin, actinomycin D, actinomycin I, actinomycin V, bafilomycin A1, bleomycin, capreomycin, chromomycin, cinoxacin, ciprofloxacin, cis-diammineplatinum(II) dichloride, coumermycin A1, L(+)-lactic acid, cytochalasin B, cytochalasin D, dacarbazine, daunorubicin, distamycin A, doxorubicin, echinomycin, enrofloxaein, etoposide, flumequnie, formycin, fumagillin, ganciclovir, gliotoxin, lomefloxacin, metronidazole, mithramycin A, mitomycin C, nalidixic acid, netropsin, nitrofurantoin, nogalamycin, nonactin, novobiocin, ofloxacin, oxolinic acid, paclitaxel, phenazine, phleomycin, pipemidic acid, rebeccamycin, sinefungin, streptonigrin, streptozocin, succinylsulfathiazole, sulfadiazine, sulfadimethoxine, sulfaguanidine purum, sulfamethazine, sulfamonomethoxine, sulfanilamide, sulfaquinoxaline, sulfasalazine, sulfathiazole, trimethoprin, tubercidin, 5-azacytidine, cordycepin, and formycin A; 2-mercaptopyridine, 4-bromocalcimycin A23187, alamethicin, amphotericin B, calcimycin A23187, chlorhexidine, clotrimazole, colistin, econazole, hydrocortisone, filipin, gliotoxin, gramicidin A, gramicidin C, ionomycin, lasalocid A, lonomycin A, monensin, N-(6-amino-hexyl)-5-chloro-1-naphthalenesulfonamide, narasin, nigericin, nisin, nonactin, nystatin, phenazine, pimaricin, polymyxin B, DL-penicillamine, polymyxin B, praziquantel, salinomycin, surfactin, and valinomycin; (+)-usnic acid, (±)-miconazole, (S)-(+)-camptothecin, 1-deoxymannojirimycin, 2-heptyl-4-hydroxyquinoline N-oxide, cordycepin, 1,10-phenanthroline, 6-diazo-5-oxo-L-norleucine, 8-quinolinol, antimycin, antipain, ascomycin, azaserine, bafilomycin, cerulenin, chloroquine, cinoxacin, ciprofloxacin, mevastatin, concanamycin A, concanamycin C, coumermycin A1, L(+)-lactic acid, cyclosporin A, econazole, enrofloxacin, etoposide, flumequine, formycin A, furazolidone, fusaric acid, geldanamycin, gliotoxin, gramicidin A, gramicidin C, herbimycin A, indomethacin, irgasan, lomefloxacin, mycophenolic acid, myxothiazol, N-(6-aminohexyl)-5-chloro-1-naphthalenesulfbriamide, nalidixic acid, netropsin, niclosamide, nikkomycin, N-methyl-1-deoxynojirimycin, nogalamycin, nonactin, novobiocin, ofloxacin, oleandomycin, oligomycin, oxolinic acid, piericidin A, pipemidic acid, radicicol, rapamycin, rebeccamycin, sinefugin, staurosporine, stigmatellin, succinylsulfathiazole, succinylsulfathiazole, sulfadiazine, sulfadimethoxine, sulfaguanidine, sulfamethazine, sulfamonomethoxine, sulfanilamide, sulfaquinoxaline, sulfasalazine, sulfathiazole, triacsin C, trimethoprim, and vineomycin A1.

The active compounds may also be administered together with antidepressants such as clozapine or olanzapine; laxatives; antidiarrheal agents; serotonin antagonists (5-HT3) such as ondansetron, clozapine or ondansetron; serotonin reuptake inhibitors (SSRIs); anti-spasmodics such as hyoscyamine or dicyclomine; proton pump inhibitors (PPIs); magnesium aluminum silicates; alverine citrate drugs; rifaximin; anti-inflammatory agents such as steroids, mesalazine (mesalamine or 5-aminosalicyclic acid); immunomodulators such as azathioprine, methotrexate, adalimumab, certolizumab, or natalizumab.

The active compounds can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an added preservative. The compositions can take such forms as suspensions, solutions or emulsions in oily or aqueous vehicles, and can contain formulatory agents such as suspending, stabilizing andior dispersing agents.

For oral administration, the active compounds can be fornuilated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, liar oral ingestion by a patient to be treated. Pharmaceutical preparations for oral use can be obtained by, for example, adding a solid excipient, optionally grinding the resulting mixture, and processing the mixture of gantries, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylppiolidone (PVP). If desired, disintegrating agents can be added, such as, but not limited to, the cross-linked polyvinyl pyrrolidone, agar, or alginic acid or a salt thereof such as sodium alginate. Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, andlor lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of such as, tablets or lozenges formulated in a conventional manner.

The active compounds can also be formulated in rectal compositions such as suppositories or retention enemas, such as containing conventional suppository bases such as cocoa butter or other glycerides.

The active compounds can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (fix example as an emulsion in an acceptable oil) or ion exchange resins, or as sparingly soluble derivatives, for example, as a sparingly soluble salt.

In transderma administration, the active compounds, for example, can be applied to a plaster, or can be applied by transdermal, therapeutic systems that are consequently supplied to the organism.

The pharmaceutical compositions of the active compounds also can comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

The present invention also provides compounds of the invention, or compositions comprising the same, for use in prophylaxis andior treatment of inflammatory diseases of the gastrointestinal tract in a patient. The present invention also provides compounds of the invention, or compositions comprising the same, for use in prophylaxis and/or treatment of inflammatory diseases of the gastrointestinal tract. The present invention also provides compounds of the invention, or compositions comprising the same, fix use in preparation of a medicament for prophylaxis and/or treatment of inflammatory diseases of the gastrointestinal tract in a patient.

The present invention also provides methods for prophylaxis and/or treatment of inflammatory diseases of the gastrointestinal tract in an animal comprising administering to the animal in need thereof an effective amount of a compound of the invention. The preseid invention also provides methods for prophylaxis and/or treatment of inflammatmy diseases of the gastrointestinal tract in an animal comprising administering to the animal in need thereof a composition of the invention. The present invention also provides methods for prophylaxis and treatment of inflammatory diseases of the gastrointestinal tract comprising administering to the animal an effective amount of a compound or salt of the invention.

The present invention also provides active compounds or compositions comprising the same, for use in prophylaxis and/or treatment of inflammatory diseases of the gastrointestinal tract in a patient The present invention also provides active compounds, or compositions comprising the same, for use in preparation of a medicament for prophylaxis andlor treatment of inflammatory diseases of the gastrointestinal tract in a patient.

The structures depicted herein may omit necessary hydrogen atoms to complete the appropriate valency. Thus, in some instances a carbon atom or nitrogen atom may appear to have an open valency (i.e., a carbon atom with only two bonds showing would implicitly also be bonded to two hydrogen atoms; in addition, a nitrogen atom with a single bond depicted would implicitly also be bonded to two hydrogen atoms). For example, "—N" would be considered b one skilled in the art to be "—NH$_2$." Thus, in any structure depicted herein wherein a valency is open, one or more hydrogen atoms, as appropriate, is implicit, and is only omitted for brevity.

Anti-Inflammatory Activities of PMX-30063 (Brilacidin) and PAX-60056 (Delparantag)

The studies discussed in the Examples demonstrate the anti-inflammatory activity of PMX-30063 and PMX-60056: inhibition of phosphodiesterase PDE4 in a POE-Glo phosphodiesterase assay: inhibition of PDE3 in a PDE-Glo phosphodiesterase assay; inhibition of TNF-α of lipopolysaccharide (LPS) induced TNF-α production in NR8383 rat macrophages; inhibition of LPS induced Monocyte Chemoattractant Prot in-1 (MCP-1) release in NR 1383 rat. macrophages; inhibition of ITS induced matrix-metalloproteinase-9 (MM -9) release in NR8383 rat macrophage (PMX-30063 only); inhibition of induced IL-6 release in NR8383 rat macrophages (PMX-30063 only). Following oral administration, PMX-30063 is taken up by the small intestine but <0.5% enters the circulation; a great advantage for treatment of intestinal epithelium with low risk of systemic toxicity. In an in vivo ulcerative colitis model, intestine weights were reduced, but not significantly, compared to untreated controls following rectal administration of PMX-30063. A dose dependent decrease in ulcerative colitis score was observed.

The present inventors hypothesize that PMX-30063 and PMX60056, as HDP mimetics, may be finictioning through the cyclic AMP/cyclic GMP pathways in suppression of proinflammatory response. PDE4 is a predominant phosphodiesterase expressed in neutrophils, T cells and macrophages and PDE4 inhibitors reduce neutrophil chemotaxis, recruitment and activation, inhibit the activation of CD4+ and CD8+ T cells, and inhibit monocytes chemotaxis. Hence, PDE4 has a broad range of .anti-inflammatory effects on various key effector cells that may be involved in ulcerative colitis and Crohn's disease. It is also recognized that use of PDE3 inhibitors can provide clinical benefit to patients' inflammatory diseases. It has shown that combining inhibitors of PDE3 and PDE4 provides greater benefits compared with inhibiting either PDE alone (Rieder et al. *PLoS One* 2013 2013;8(2):e56867. doi: 10.1371Journal.pone. 0056867. Epub 2013 Feb. 28).

METHODS

Set forth below is a discussion of the research methods referred to in the Examples with references to the figures that are part of the present application.

Method for FIG. 1. Phosphodiesterase inhibition assays of PD34 were performed, using PMX-30063. The PDE-Glo phosphodiesterase assay (Promega, Madison, Wis., USA Catalog No. V1361) was performed using 8 ng of PDE4B, 1 µM cAMP substrate and PMX-30063. The compounds and PDE4B (BPS Biosciences, San Diego, Calif.) were mixed and pre-incubated at room temperature for 15 minutes. Substrate was added and the reaction was incubated for 7 minutes at room temperature. Data are presented as luminescence units (RLU).

Figure 2:
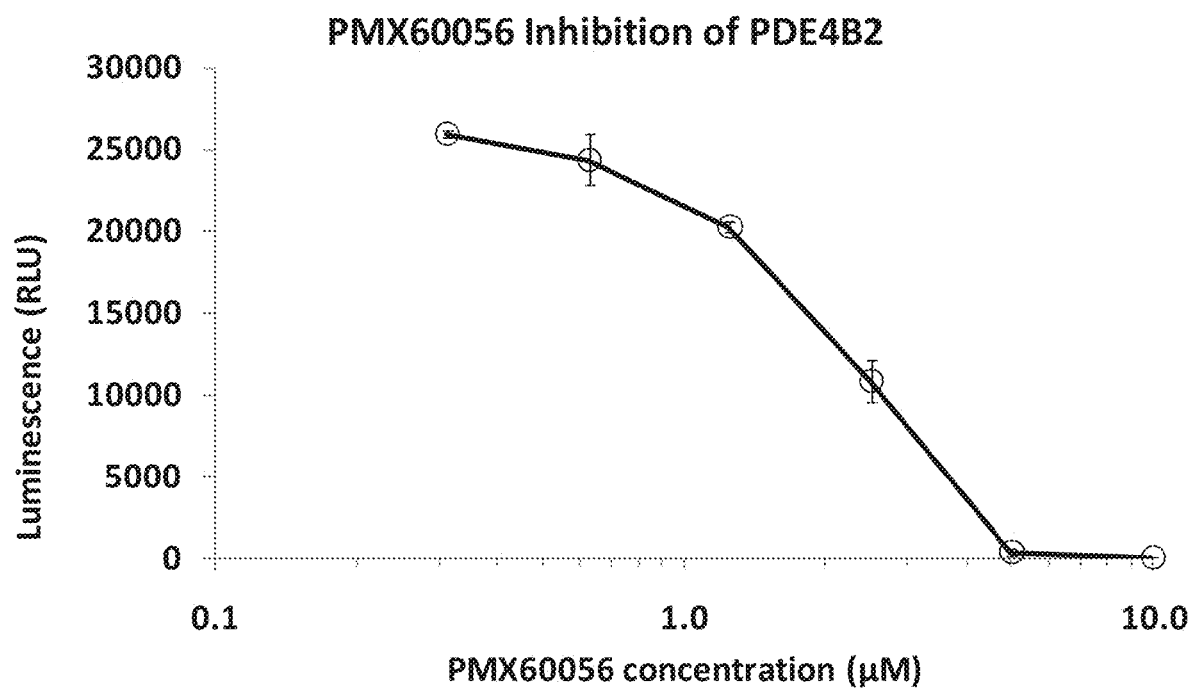
FIG. 2 illustrates that PMX-60056 inhibited PDE4 with an IC50 in the 3 µM range (n=5).

Method for FIG. 2. Phosphodiesterase inhibition assays of PDE4 were performed, using PMX-60056. The PDE-Glo phosphodiesterase assay (Promega, Madison, Wis., USA Catalog No, V1361) was performed using 8 ng of PDE4B (BPS Biosciences, San Diego, Calif.), 1 µM cAMP substrate and PMX-30063. The compounds and PDE4B were mixed and pre-incubated at room temperature for 15 minutes. Substrate was added and the reaction was incubated for 7 minutes at room temperature. Data are presented as luminescence units (RLU).

Figure 3:
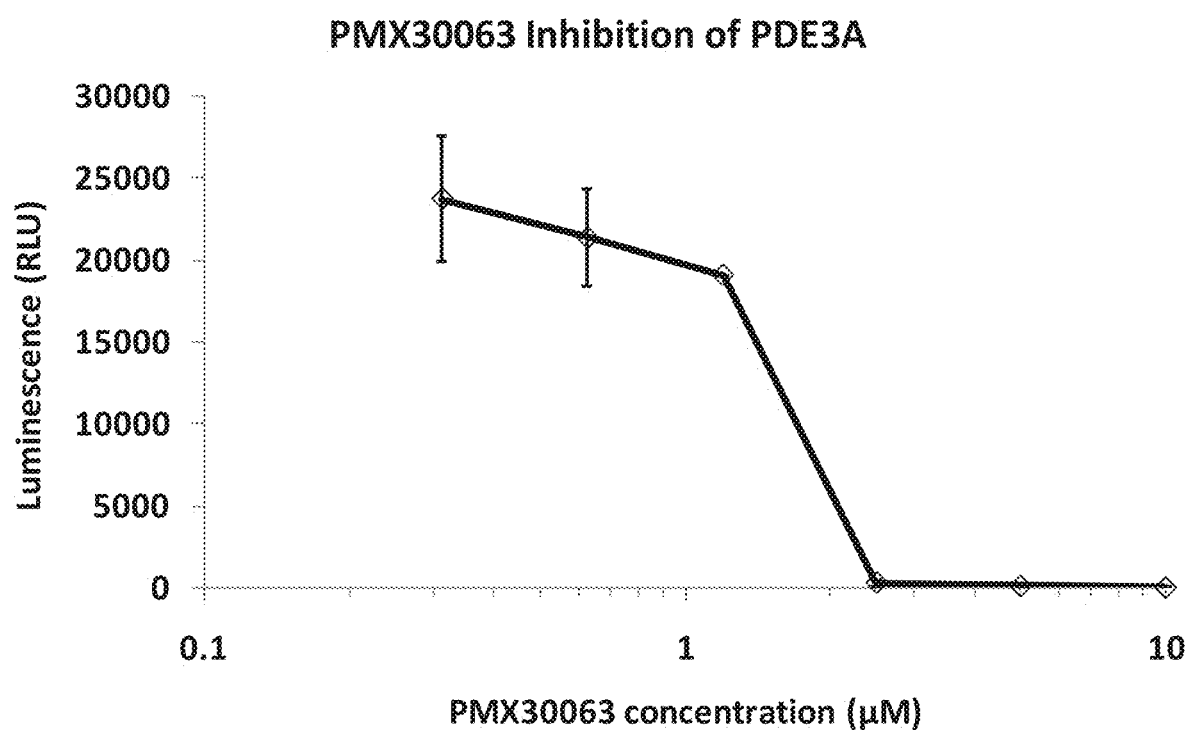
FIG. 3 illustrates that PMX-30063:inhibited PDE3 at an IC50 of 1.5±0.2 µM (n=4).

Method for FIG. 3. Phosphodiesterase inhibition assays of PDE3 were performed using PMX30063. The PDE-Glo phosphodiesterase assay (Promega, Madison, Wis., USA Catalog No, V1361) was performed according to manufacturer's instruction using 2.75 ng of PDE3A, 1 µAM cAMP substrate and PNLX-30063. The compounds and PDE3A were mixed and pre-incubated at room temperature for 15 minutes. Substrate was added and the reaction was incubated for 7 minutes at room temperature. Data are presented as luminescence units (RLU).

Figure 4:
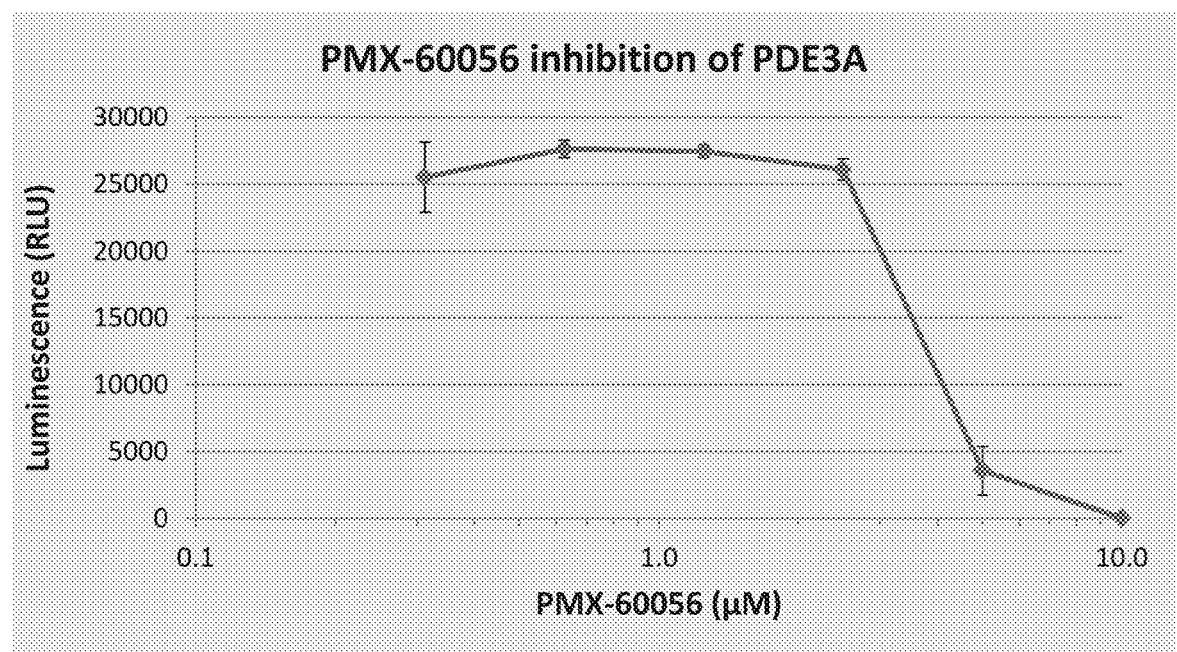
FIG. 4 illustrates that PMX-60056 inhibited PDE3 at an IC50 of 3 µM.

Method for FIG. 4. Phosphodiesterase inhibition assays of PDE3 were performed using PMX-60056. The PDE-Glo phosphodiesterase assay (Promega, Madison, Wis., USA Catalog No. V1361) was performed according to manufacturer's instruction using 2.75 ng of PDE3A, 1 µM cAMP substrate and PMX60056. The compounds and PDE3A were mixed and pre-incubated at room temperature for 15 minutes. Substrate was added and the reaction was incubated for 7 minutes at room temperature. Data are presented as luminescence units (RLU).

Figure 5:
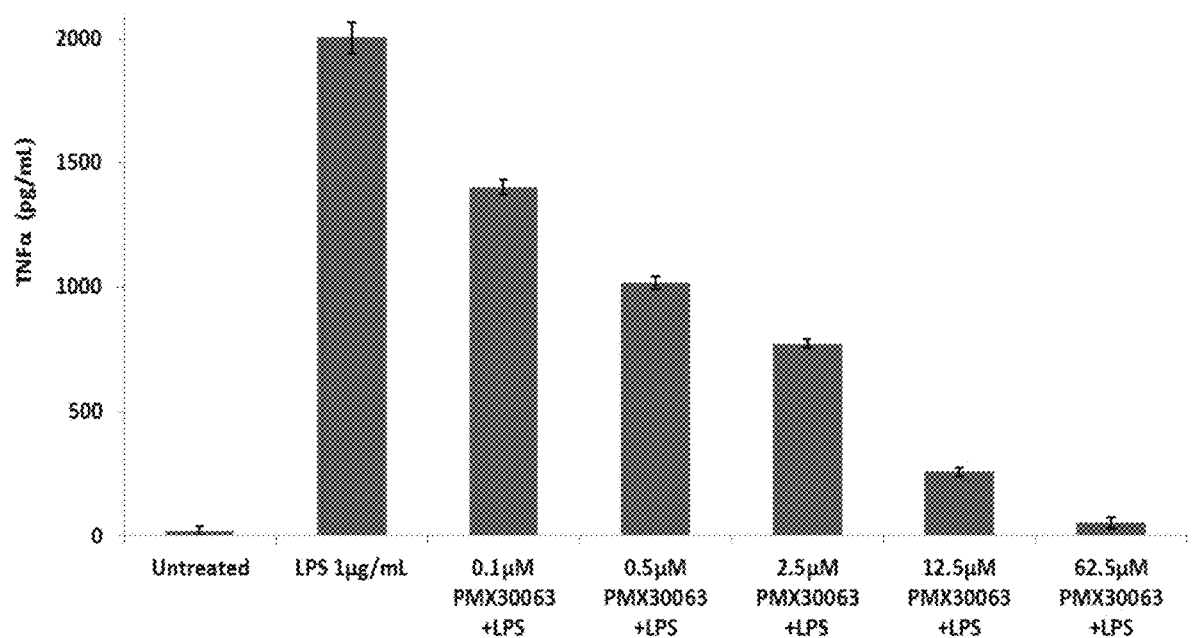
FIG. 5 illustrates that PMX-30063 inhibited the LPS-induced TNF-α production in rat macrophages.

Method for FIG. 5. TNF-alpha assays were performed using PMX-30063. NR8383 (CRL-2192, ATCC, Manassas, Va.) rat macrophage cells were pretreated with PMX-30063 for 45 minutes followed by treatment with 1 µg/Ml Lipopolysaccharides (LPS) from E. coli (Signa, St. Louis, Miss.) for 8 hours. INF-α concentrations in the supernatants were determined by ELISA using an immunoassay kit specific for rat TNF-α (R&D Systems, Minneapolis, Minn.) according to manufacturer's instructions.

Figure 6:
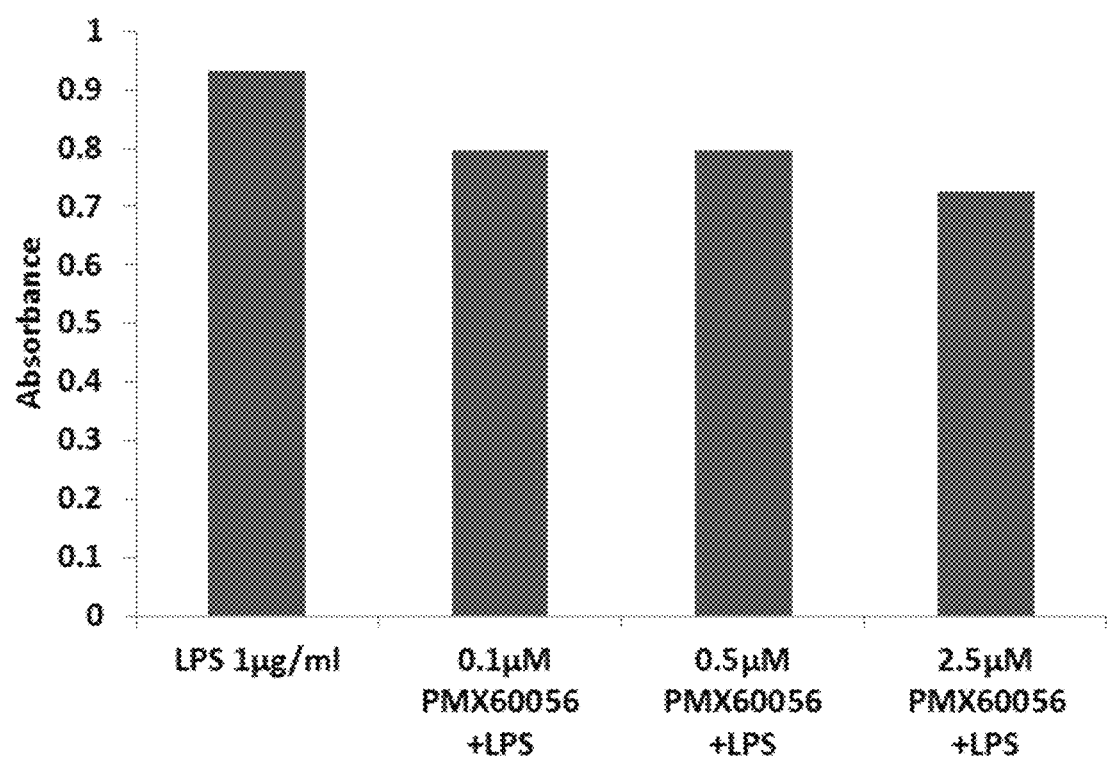
FIG. 6 illustrates that PMX-60056 inhibited the IPS-induced TNF-α production in rat macrophages.

Method for FIG. 6. TINF-alpha assays were performed using MX-60056. NR8383 rat macrophage cells were preheated with NL -60056 for 45 minutes followed by treatment with 1 µg/ml LPS from E. coli. (Sigma, St. Louis, Miss.) for 8 hours. TNF -α concentrations in the supernatants were determined by ELISA using an immunoassay kit specific for rat INF-α (R&D Systems Minneapolis. Minn.) according to manufacturer's instructions.

Figure 7:
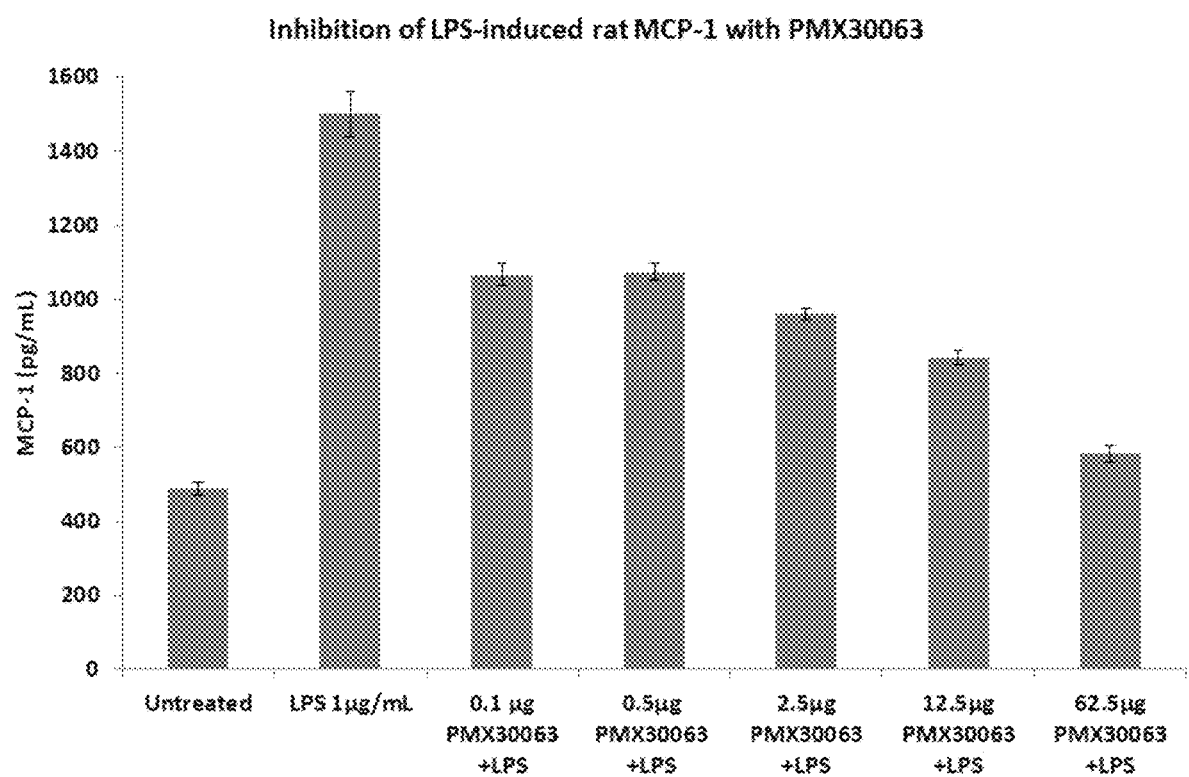
FIG. 7 illustrates that PMX-30063 inhibited MCP-1 induction after LPS stimulation of rat macrophages with a minimum of a 25% decrease in MCP-1 levels at 0.5 µM.

Method for FIG. 7. MCP-1 assays were performed using PMX-30063. Rat macrophages (NR8383) were pretreated with PMX-30063 with concentrations shown for 45 minutes, followed by 1 µg/ml LPS treatment from E. coli (Sigma, St. Louis, Miss.) for 8 hours. After 8 hours, supernatants were collected for MCP-1 measurement by ELISA, MCP-1 was measured using an immunoassay kit according to manufacturer's instructions (Thermo Scientific, Rockford, Ill.).

Figure 8:
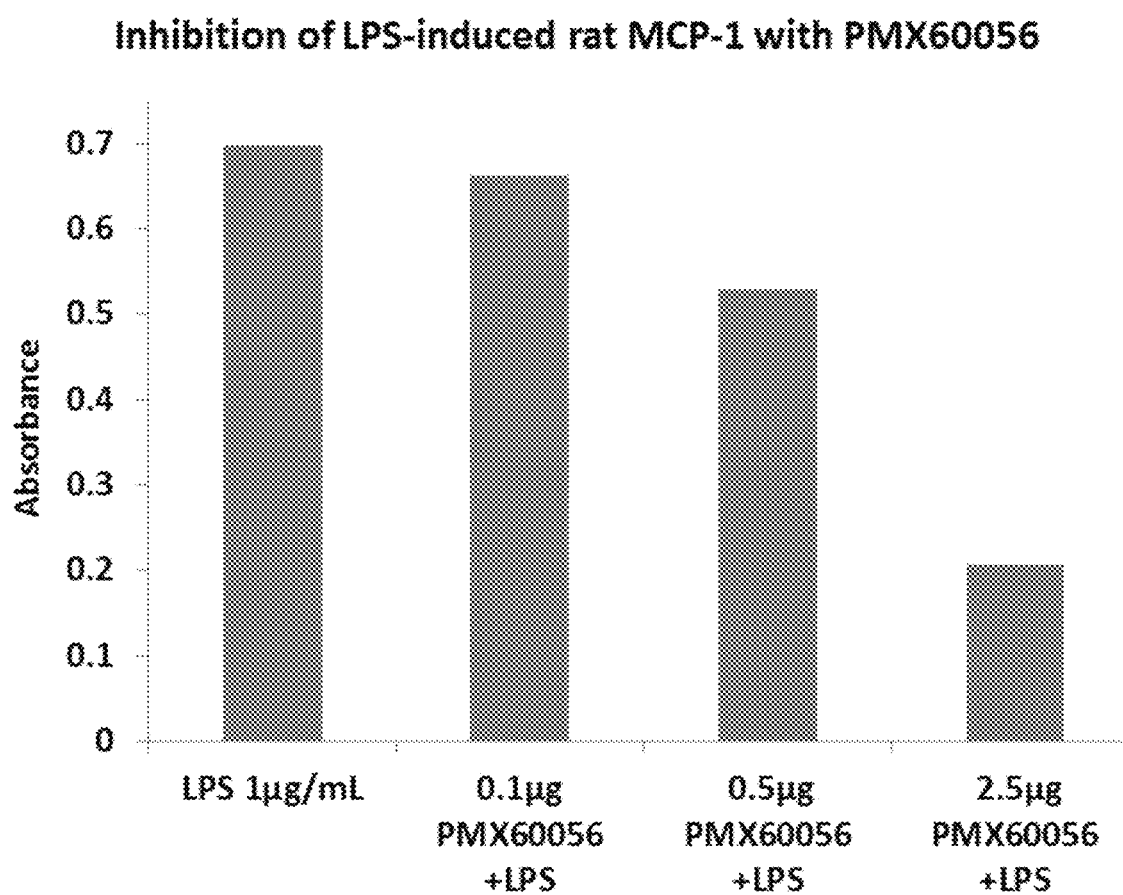
FIG. 8 illustrates that PMX-60056 inhibited MCP-1 induction after LPS stimulation of rat macrophages with a minimum of 25% decrease in MCP-1 levels at 0.5 µM.

Method for FIG. 8. MCP-1 assays were performed using PMX-60056. Rat macrophages (NR8383) were pretreated with PMX30063 with concentrations shown for 45 minutes, followed by lugliul LPS treatment from E. coli (Sipna, St. Louis, Miss.) for 8 hours, After 8 hours, supernatants were collected for MCP-1 measurement by ELISA. MCP-1 was measured using an inunimoassay kit according to manufacturer's instructions (Thermo Scientific, Rockford, Ill.).

Figure 9:
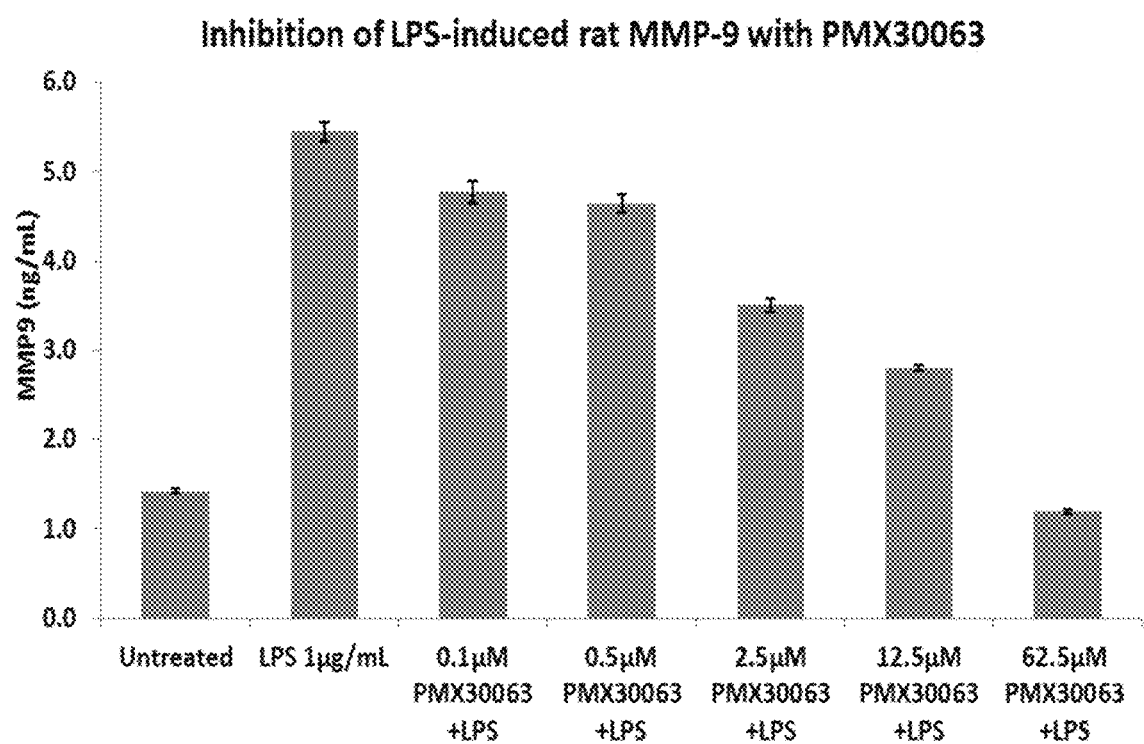
FIG. 9 illustrates that after LPS stimulation of rat macrophages a 50% decrease in MMP-9 levels at a 12.5 µM concentration of PMX-30063 was observed.

Method for FIG. 9. MMP-9 assays were performed using PKK-30063. Rat macrophages (NR8383) were pretreated with PMX-30063 with concentrations shown for 45 minutes, followed by 1 µg/ml LPS treatment from E. coli (Sipna, St. Louis, Miss.) for 8 hours. After 8 hours, supernatants were collected for MMP9 measurement by ELISA using immunoassay kit (R&D Systems, Minneapolis, Minn.) according to manufacturer's instructions.

Figure 10:
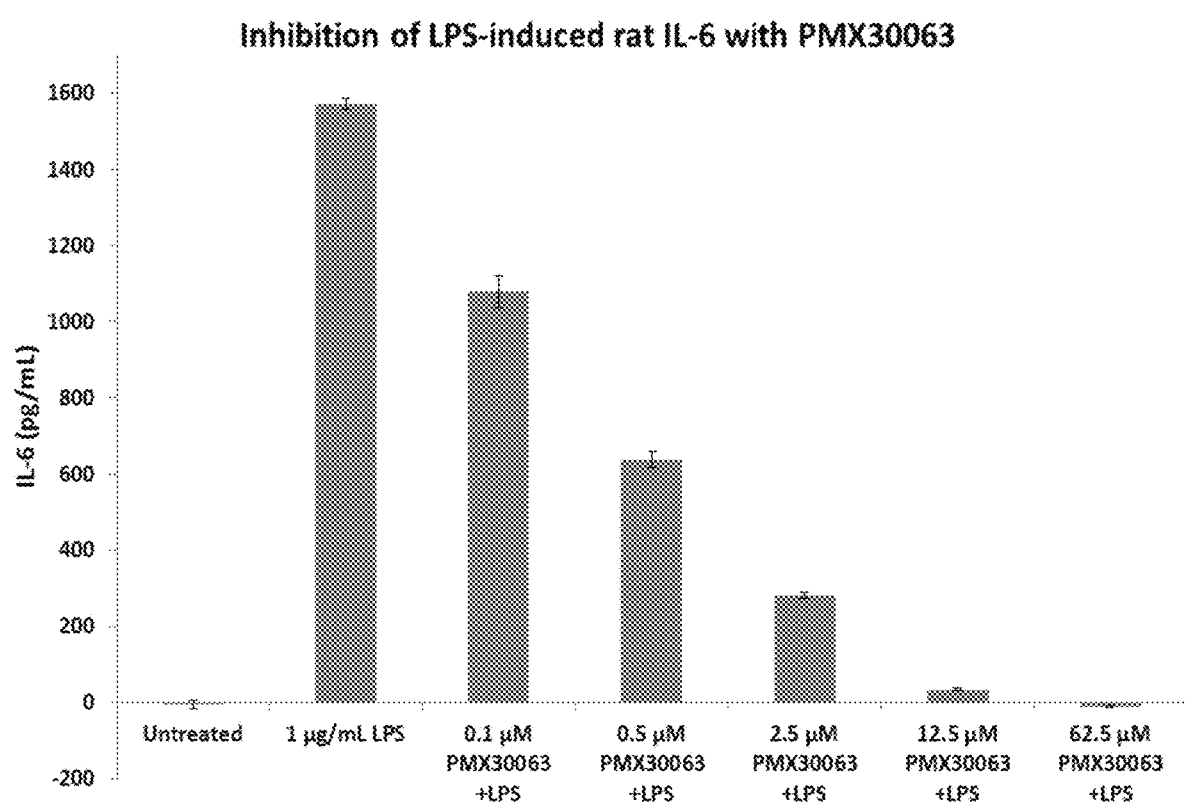
FIG. 10 illustrates that PMX-30063 inhibited IL-6 induction after LPS stimulation of rat macrophages with about a 50% decrease in IL-6 levels at a 0.5 µM of PMX-30063 being observed.

Method for FIG. 10. IL-6 release assays were performed using PMX-30063. Rat macrophages (NR8383) were pretreated with PMX-30063 with concentrations shown for 45 minutes, followed by lugliul LPS treatment from E. coli (Sipria, St. Louis, Miss.) for 8 hours. After 8 hours, supernatants were collected for IL-6 measurement by ELISA using immunoassay kit (R&D Systems, Minneapolis, Minn.) according to manufactuivr's instructions.

Figure 11:
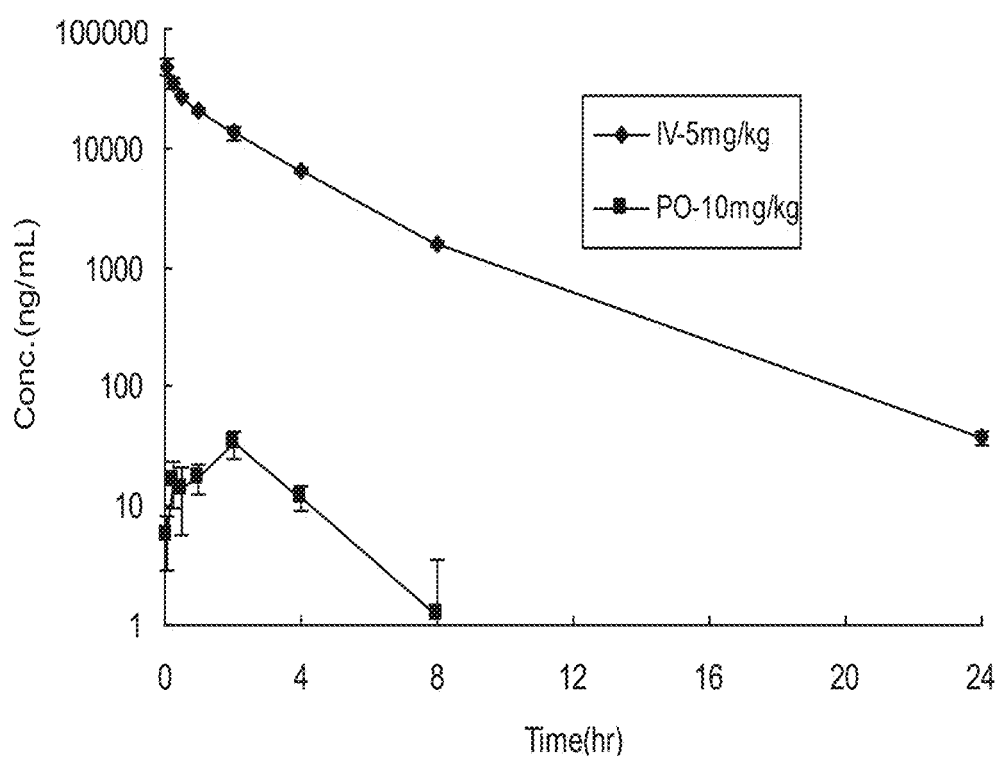
FIG. 11 illustrates that when PMX-30063 was evaluated for plasma and small intestine concentration following 10 mg/kg given orally or 5 mg/kg given IV in male Balb/c mice, the peak concentration of PMX60073 given IV was 48,415 ng/mL whereas, peak concentration in plasma was 33.7 ng/ML when given PO.

Method for FIG. 11. PMX-30063 was evaluated for plasma concentration following oral (PO) or intravenous (IV) administration in male Balb/c mice (Study 16009-12001). The test article, PMX-30063, was corrected for salt form but no adjustment was made for purity. PMX-30063 was dissolved in dissolved in half volume of water, then is added half volume of 2X saline to yield nominal concentration of 1 mg/mL for oral administration.

The resulting formulation was clear colorless solution (pH 7) and was stored at room temperature until administered. The formulated solution was clear and colorless until dosing was completed. The concentration of PMX-30063 in dosing solution was confirmed by HPLC-UV with accuracy of 95.5%.

A total of 60 male Balb/c mice, approximately 4-7 weeks' of age at receipt with body weight of 18.0 g to 21.9 g were used in this study. The test article, PMX-30063, was administered orally at 10 mg/kg in 10 mL/kG or intravenously at 5 mg/kg at 5 mL/kg volume via a single bolus administration.

Three mice in each group were used for blood at each time point at post-dose at 5 minutes. 15 minutes, 30 minutes, 1, 2, 4, 8, and 24 hours for Groups 1-2. Blood samples (at least 300 µL/sample were collected via cardiac puncture after euthanasia by carbon dioxide inhalation at appropriate time points. Samples were placed in tubes containing $K_2$-EDTA, and then centrifuged at approximately 8,000 rpm for 6 minutes at 4° C. and the resulting plasma were separated and stored frozen at approximately −80° C.

The pharmacokinetic (PK) analysis were conducted by Medicilon Preclinical Research (Shanghai) LLC. The PK parameters were determined by the Study Director for the test article from mean concentration-time data in the test species. A non-compartmental module of WinNonlin™ Professional 5.2 was used to calculate parameters. Any BLQs (LLOQ=2.5 ng/mL for plasma and LLOQ=500 ng/g for small intestine) were replaced with a value of "0", and the mean value and its standard deviation (SD) are calculated with these replaced values.

Plasma samples (50 µL) were transferred to centrifuge tube, then 250 µL IS solution (50 ng/mL Carvedilol) was added to it. After vortexing for 1 minute and centrifuging for 5 minutes at 15,000 rpm, 100 µL aliquots of supernatant were transferred to glass autosampler vials.

Figure 12:
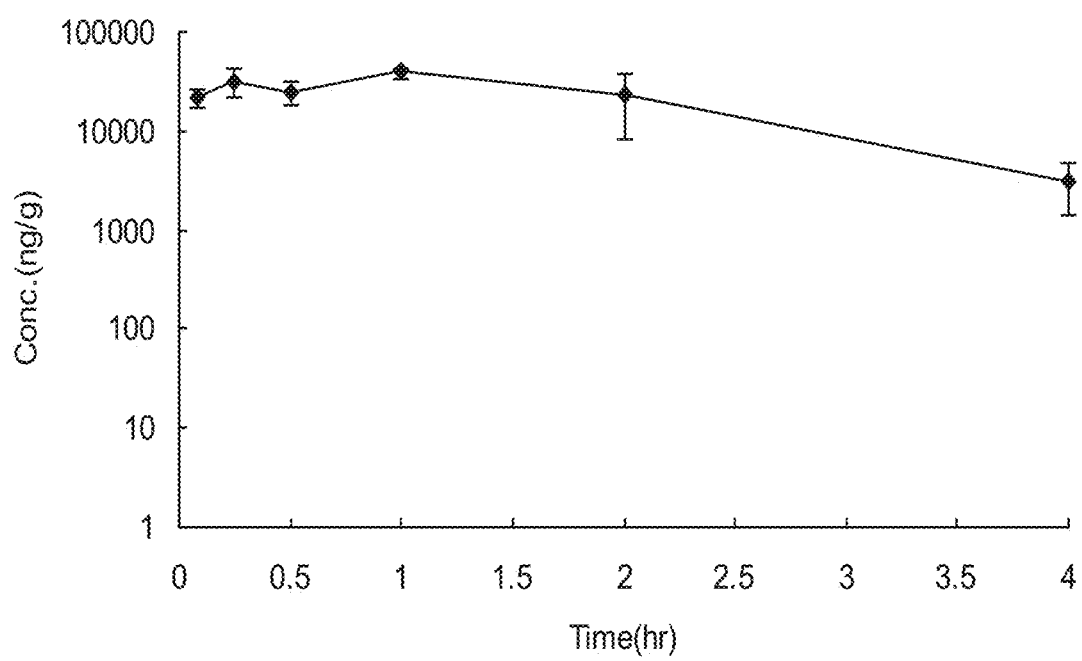
FIG. 12 illustrates that when PMX-30063 was evaluated for plasma and small intestine concentration following 10 mg/kg given orally or 5 mg/kg given IV in male Balb/c mice (Study 16009-12001). after PO administration, the peak concentration in the small intestine tissue was 38,941 ng per grain of tissue.

Method for FIG. 12, PMX-30063 was also evaluated for extent of tissue distribution following oral (PO) or intravenous (IV) administration (PO) in male Balb/c mice (Study 16009-12001). PNLX-30063 was prepared and administered as described in FIG. 11. The small intestine with content of each animal for were harvested and placed per animal per tissue into a tube. The small intestine with content samples were snap frozen in dry ice and then stored at −80° C. until bioanalysis. All the samples were labeled with detailed information such as study number, animal number, matrix, and time points of collection and date of collection. In addition, the extra animals obtained for the study, but not placed on study were used for collection of small intestine with content. The resulting small intestine with content samples were then applied to the development of the bioanalytical method and sample bioanalysis in this study. Bioanalytical analysis was performed on samples by LC-MS/MS.

For analyzing the contents of the small intestine, small intestine samples were homogenized by adding saline (1 g small intestine: 5 mL saline). Small intestine homogenates (50 µL) were transferred to tubes and 250 µL internal standard (IS) working solution (50 ng/ML Carvedilol) was added to each sample. After vortexing for 1 minute and centric tging for 5 minutes at 15,000 rpm, 100 µL aliquots of supernatant were transferred to glass autosampler vials.

Figure 13:
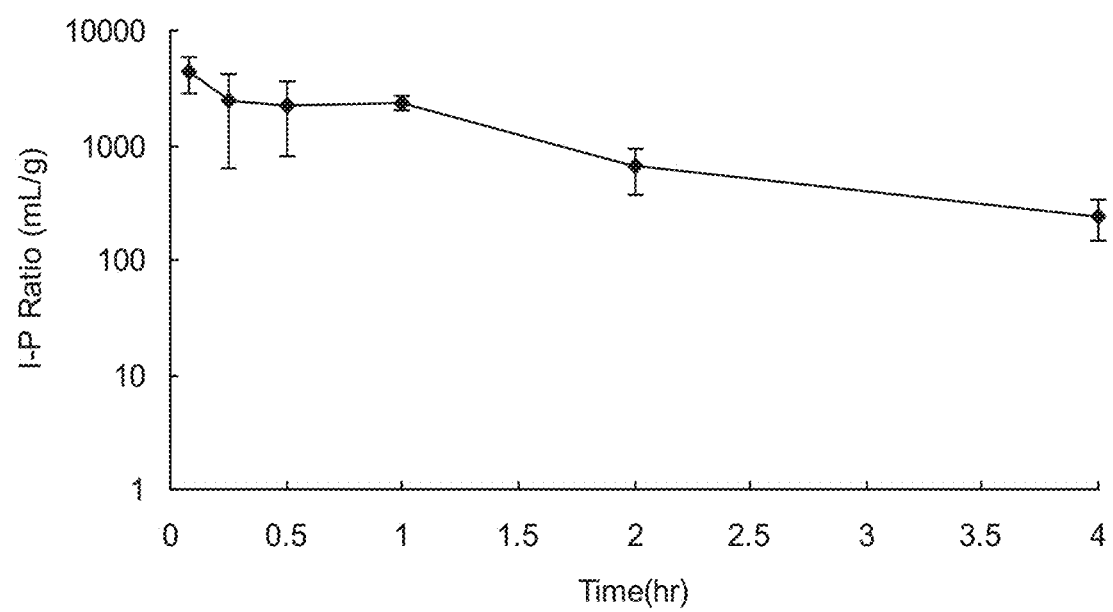
FIG. 13 illustrates the intestine/plasma concentration ratio following oral administration of PMX-30063 calculated based on data derived from FIGS. 12 and 13.

Method for FIG. 13. Intestine/plasma concentration ratio following oral administration of PMX-30063 was calculated based on data derived from FIGS. 11 and 12. The ratios versus time are shown.

Figure 14:
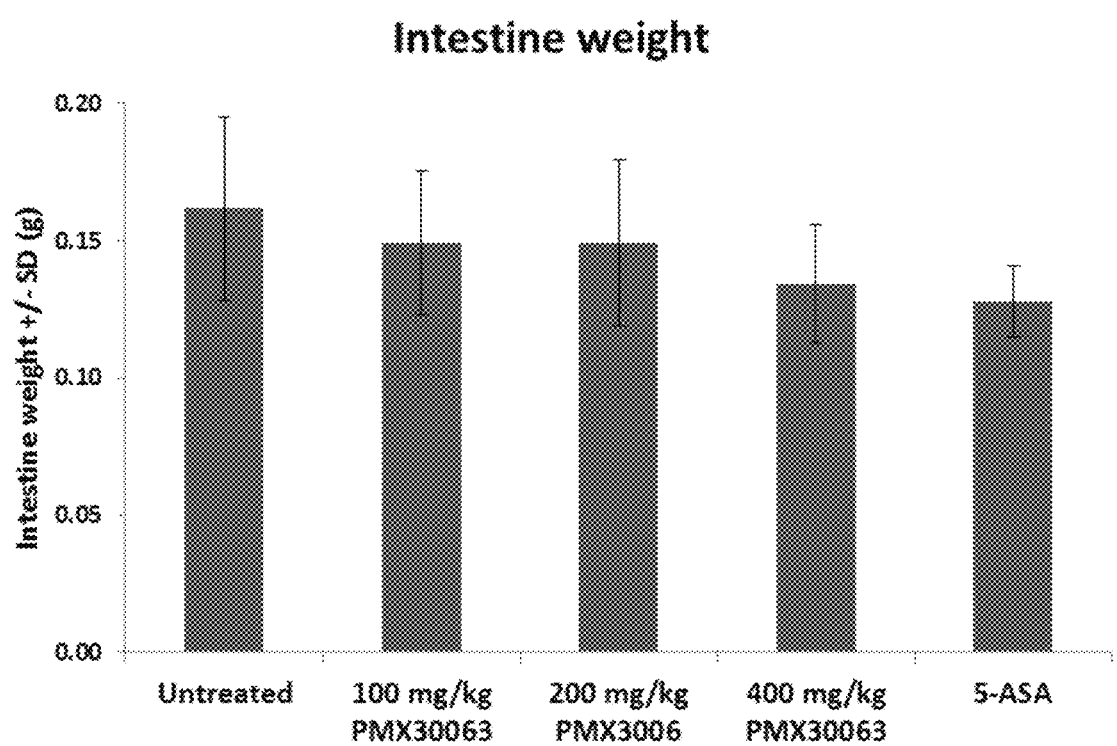
FIG. 14 illustrates that in an in vivo ulcerative colitis model, intestine weights were reduced, but not significantly, compared to untreated controls following rectal administration of PMX-30063.

Method for FIG. 14. PMX-30063 was evaluated for efficacy in an ulcerative colitis (UC) model. Balb/c mice were fasted for 24 hours. Ulcerative colitis was induced by injecting 200 µL of 4% acetic acid into the rectum. Four days later, animals were treated once daily for 4 days with PMX-30063 at either 100 mg/kg, 200 mg/kg or 400 mg/kg intrarectally. Another group of animals were treated with 5-ASA (5-aminosalicylic acid or esalamine), and another received no treatment. Seven days after the first dose, five cm of intestine were cleaned in cold saline then weighed.

Figure 15:
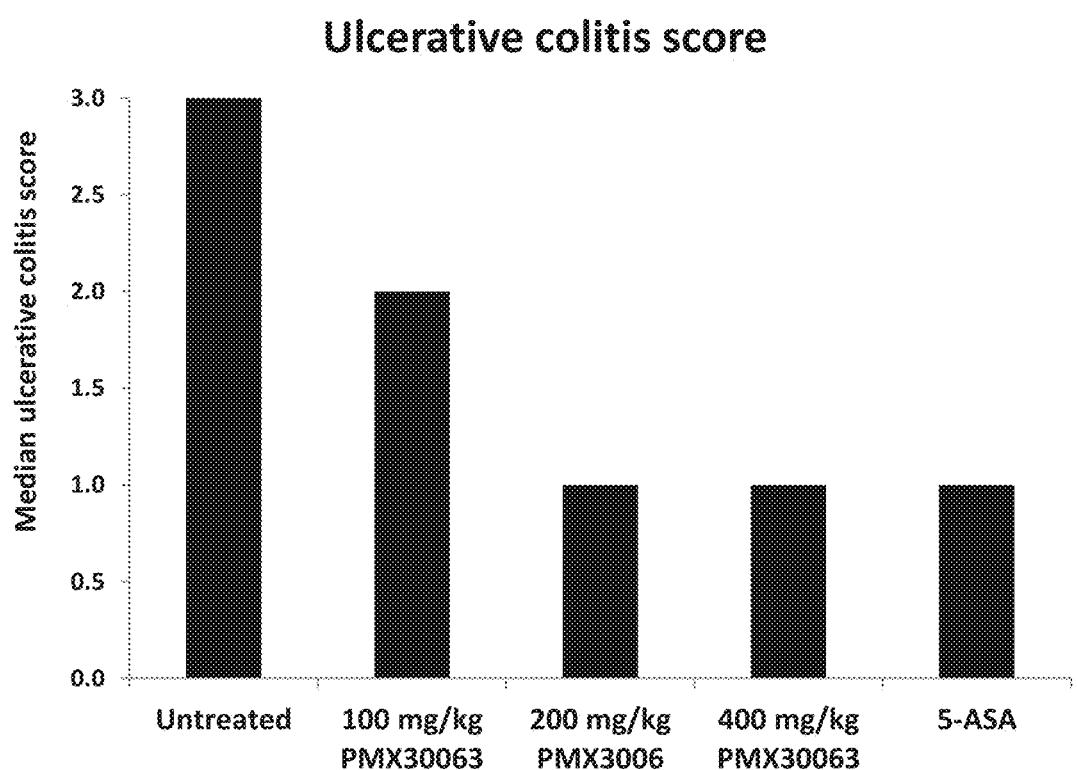
FIG. 15 illustrates that a dose dependent decrease in ulcerative colitis score following rectal administration of PMX-30063 was observed; however, only in animals treated with 400 mg/kg was the score significantly reduced compared to untreated controls; and that animals treated with 5-ASA showed no significant efficacy.

Method for FIG. 15. PMX-30063 was evaluated for efficacy in an ulcerative colitis (UC) model. Balb/c mice were fasted for 24 hours. Ulcerative colitis was induced by injecting 200 µL of 4% acetic acid into the rectum. Four days later, animals were treated once daily for 4 days with PMX-30063 at either 100 mg/kg, 200 mg/kg or 400 mg/kg intrarectally. Another group of animals were treated with 5-ASA (5-aminosalicylic acid or esalamine), and another received no treatment. Seven days after the first dose the colon was examined visually for ulcerative colitis and scored according to the Table below.

| Ulcerative Colitis Score | Observation |
|---|---|
| 0 | no damage |
| 1 | localized damage with ulcers |
| 2 | linear ulcers without severe inflammation |
| 3 | linear ulcers with inflammation at one point |
| 4 | sores or inflammation at two or more points |
| 5 | large ulcer or inflammation more than 1 centimeter |

In order that the invention disclosed herein may be more efficiently understood, examples are provided below. It should be understood that these examples are for illustrative purposes only and are not to be construed as limiting the invention in any manner. Throughout these examples standard techniques, were carried out using commercially available reagents, except where otherwise noted. Brilacidin and delparantag, which were tested as described in the Examples, were prepared by their respective suppliers by the methods described in Examples 1 and 2 respectively, based on the respective disclosures in U.S. patent application Ser. No. 13/661,466 filed Oct. 26, 2012 and U.S. Pat. No. 8,354,556 issued Jan. 15, 2013, Brilacidin was obtained from Johnson Matthey Pharma Services, Devens, Mass. and Delparantag was obtained from Ricerca Biosciences, Concord, Ohio.

The following abbreviations have been used for common solvents: THF, tetrahydrofuran; DMA, dimethyacetamide; DMSO, dimethylsalphoxide; DMF, dimethylformamide; EtOAc, ethyl acetate; TFA, trifluoroacetic acid; DCM, dichloromethane ; MTBE, t-butylmethyl ether.

EXAMPLES

Example 1: Preparation of Brilacidin (PMX-30063)

Scheme 1: Synthetic methodologies for the preparation of PMX-30063

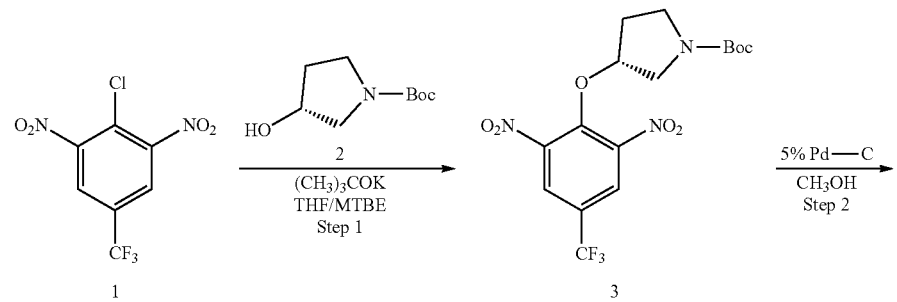

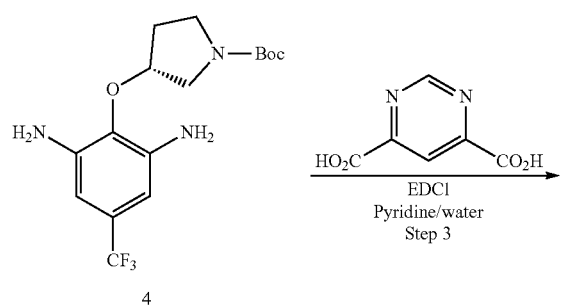

-continued
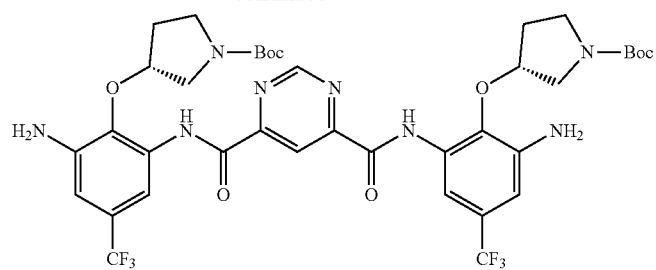
5
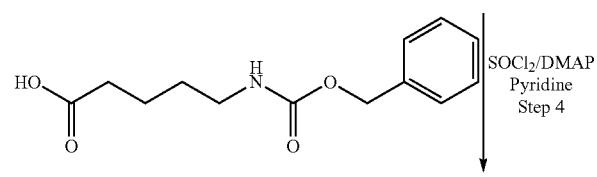
SOCl₂/DMAP
Pyridine
Step 4
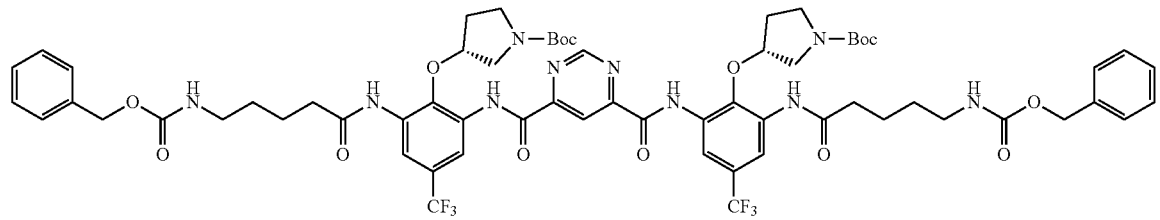
6
H₂/10% Pd—C | Step 5
CH₃OH
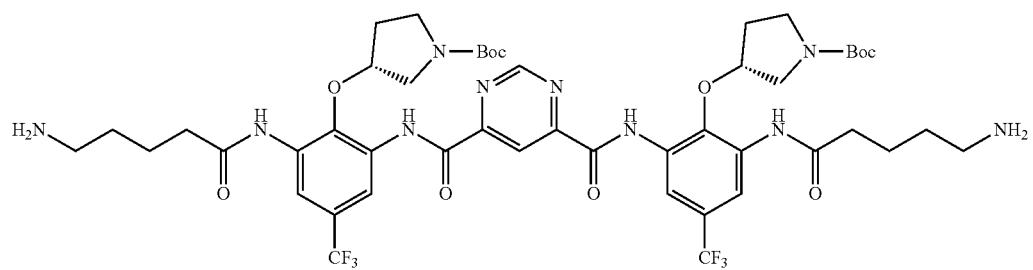
7
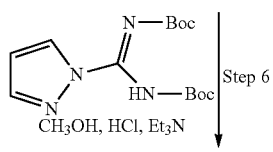
CH₃OH, HCl, Et₃N | Step 6

-continued

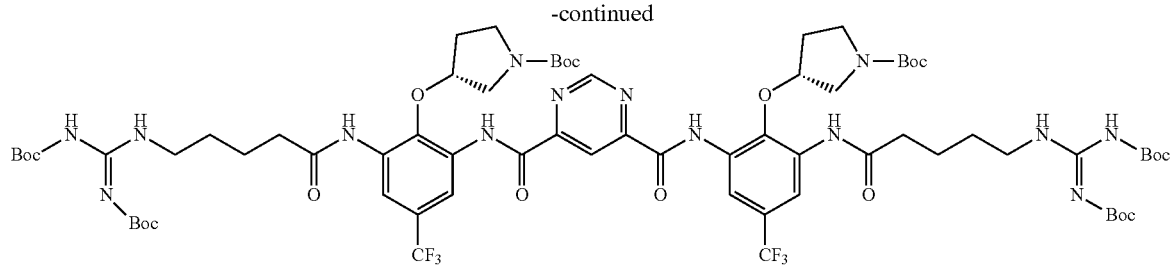

8

HCl/EtOAc, 20 equiv. H₂O | Step 7

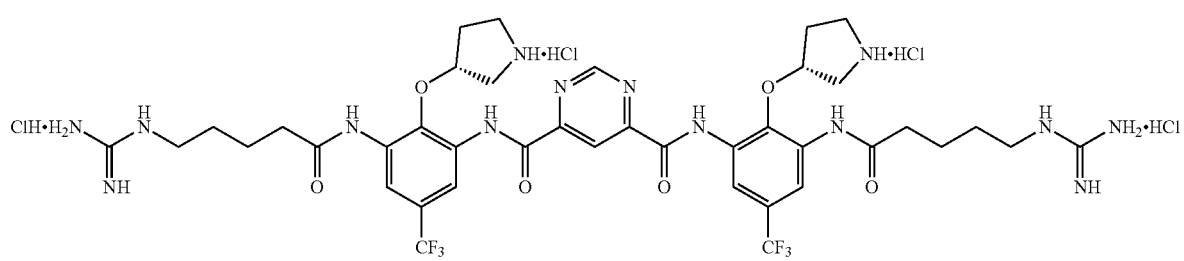

Brilacidin (PMX-30063)

Step 1: N-Boc-3-pyrrolidinol (2.2 kg) is ssolved tetrahydrofuran (11.2 kg and cooled to 10° C. Then potassium tert-butoxide (1.5 kg) is added, followed by addition of a solution of 2-chloro-5-(trifluoromethyl)-1,3-dinitrobenzene (3.0 kg) in t-butylmethyl ether (5.1 kg). The resulting mixture is stirred for 16 hours at 10-17° (and t-butylmethyl ether (10.7 kg) and water (15.6 kg) are then added. The organic layer is separated and washed by brine and evaporated to dryness. The crude product on crystallization with ethanollwater twice gives 2.17 kg (46.3%) of (R)3-(2,6-dinitro-4-trifluoromethylphenoxy)pyrrolidine-1-carboxylic acid tert-butyl ester (3) with expected HPLC purity of about 96.4%.

Step 2: 2.2 kg of compound 3 is dissolved in methanol (6.1 kg), and then 5% Pd-C (294 g) is added under nitrogen. The resulting reaction mixture is stirred under hydrogen at 10-15 psi for 98 hours. Reaction progress is monitored by HPLC. The reaction mixture is filtered through a Celite pad and filtrate is concentrated to afford 1.715 kg (89.5%) of (R)-3-(2,6-diamino-4-trifluoromethylphenoxy)-pyrrolidine-1-carboxylic acid tert-butyl ester (4) with expected HPLC purity of about 96.2%.

Step 3: Compound 4 (1.6 kg) is coupled with pyrimidine-4,6-dicarboxylic acid (383 g) in the presence of 1-[(3-(dimethylamino)-propyl)]-3-ethylcarbodiimide hydrochloride (1.29 kg), in pyridine, under inert atmosphere, at ambient temperature. After 25 hours, the reaction mixture is diluted in water (92 kg), a solid is separated out, which is collected by filtration and dried at 37-40° C., and crude compound is purified by trituration with ethyl acetate/heptanes for three times. Yield: 1.34 kg (70%), expected Purity about: 87.5%.

Step 4: The solution of 1.07 kg of DMAP in 16.9 kg anhydrous pyridine is cooled to 0° C. with ice bath. 1050 g of thionyl chloride is added slowly and the temperature is kept below 15° C. Once the solution reaches 5° C. 5-N-(carbobenzoxyamino)valeric acid (2.2 kg) is added and temperature is kept below 15° C. The solution is cooled to 5° C. and followed by addition of compound 5 (2.5 kg) and stirring is continued for 22 minutes before the temperature is brought up to room temperature. The resulting reaction mixture is stirred for 21 hours, then ethyl acetate (17.3 kg) is added. The organic layer is washed with 1,2N sodium hydroxide, then with sodium chloride and dried over sodium sulfate. The organic layer is separated and evaporated to dryness, and resulting residue on trituration with toluene gives crude compound 6, which is purified by silica gel chromatography using methanol/ethyl acetate as eluent. Compound 6 is further purified by recrystallization from did Lim mil-ethane/toluene mixture. Yield: 1.47 kg (30%), expected HPLC purity: about 97.6%.

Step 5 and 6: Compound 6 (1.47 kg) is dissolved in methanol (11.6 kg), then 10% Pd-C (143 g) is added under nitrogen atmosphere. The resulting reaction mixture is stirred 2.5 hours under hydrogen at ambient pressure, and then catalyst is removed by filtration. To the filtrate, 1N HCl (2L), triethylamine (420 g) and di-boc-guanylpyrazole (0.70 g) are added in order. The resulting reaction mixture is stirred at room temperature for 102 minutes. Then it is evaporated, followed by dilution with ethyl acetate (10.7 kg). The organic layer washed with sodium chloride solution, dried over sodium sulfite and evaporated to dryness. The crude compound 8 is purified by column chromatography with 1.9 kg of silica gel and ethyl acetate/dichloromethane to methatiordichloromethane. Yield: 1.19 kg (62.3%). expected HPLC purity: about 96.4%.

Step 7: Compound 8 (1.17 kg) is dissolved in ethyl acetate ((21.5 kg) and 281 g of water is added. HCl gas is added to the solution while the temperature is kept below 45° C. After 5 hours, the reaction is found to be complete. The solid (PNLX-30063, brilacidin) is collected by filtration. Further purification of PMX-30063 is done by trituration of above solid with methanol/THF. Yield: 696 g (84.1%), expected HPLC purity: about 98.6%.

Scheme 2-Synthetic strategies for the preparation of PMX-60056
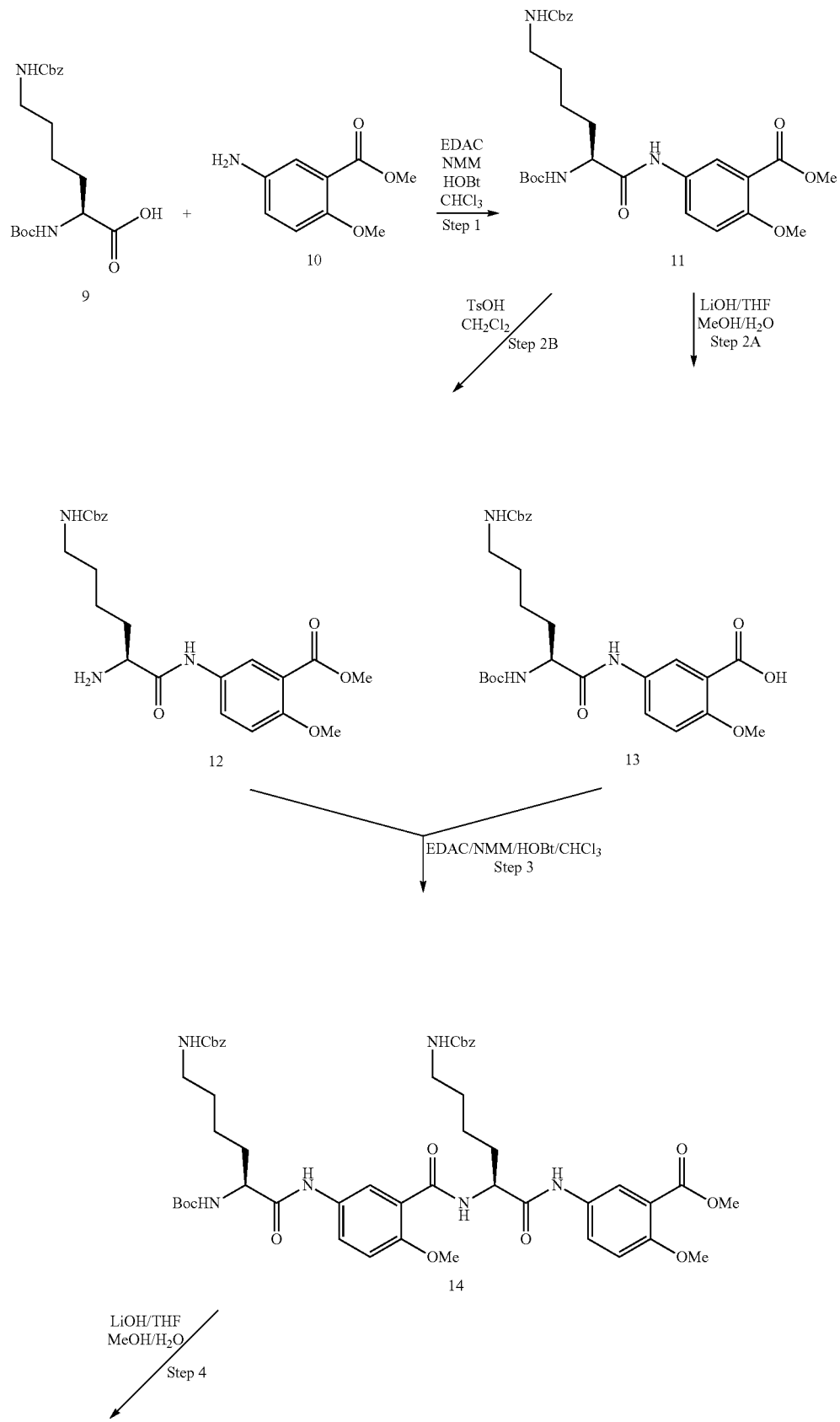

-continued
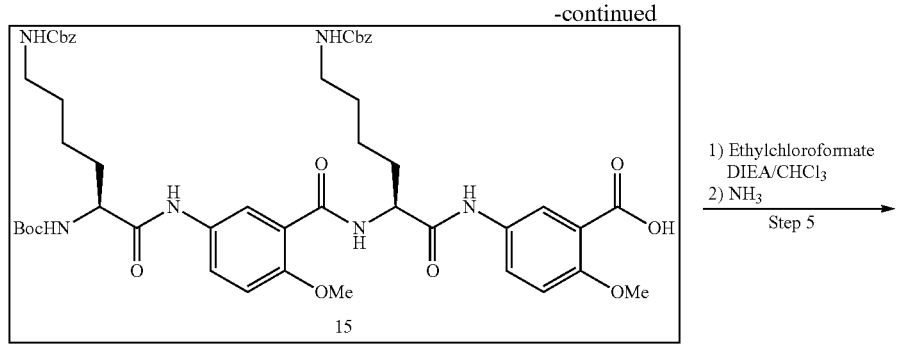
Split Compound for use in steps 5 and 7
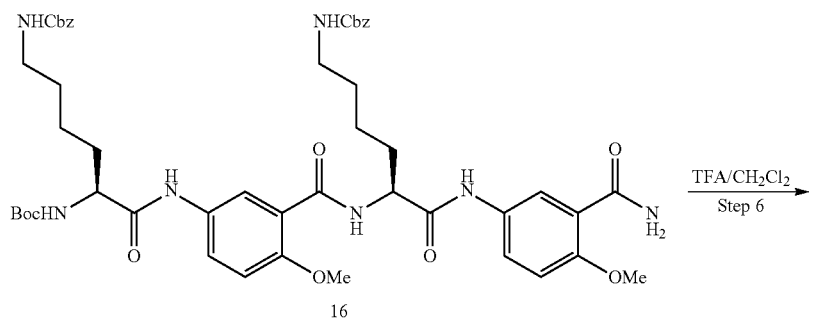
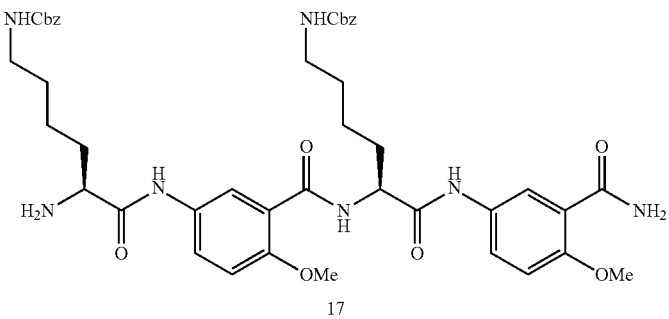
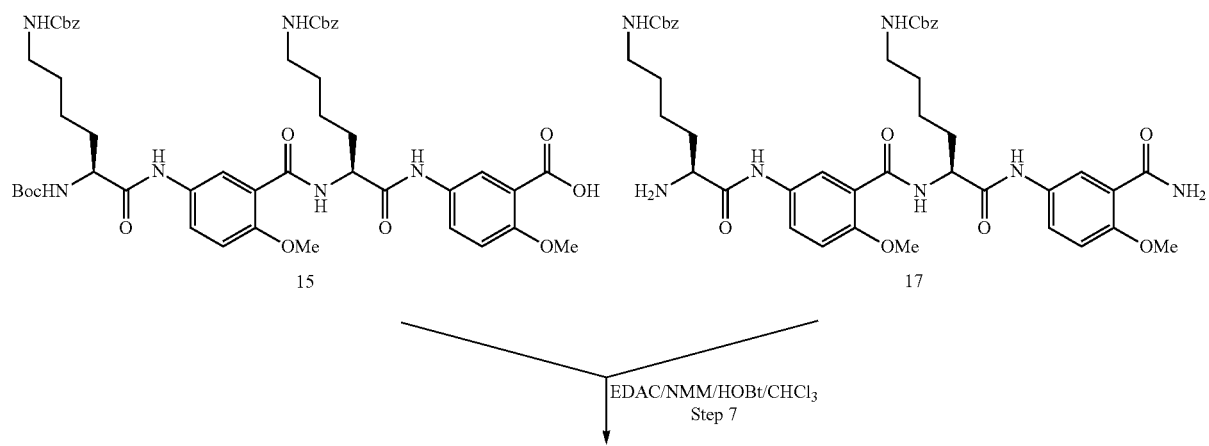

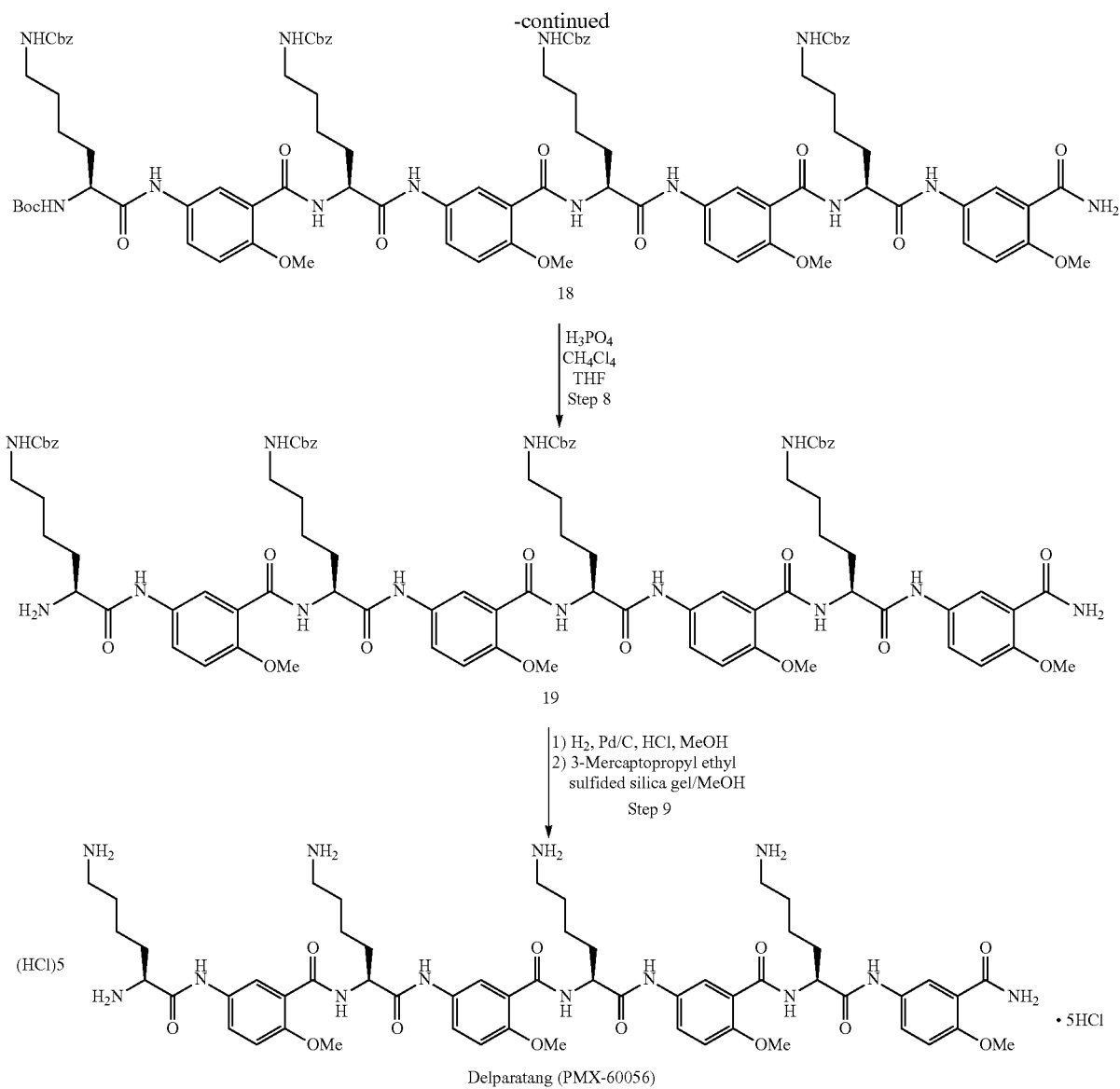

Step 1: Preparation of Compound 11

A mixture of compound 9 (1665 g, 4.379 mol, 1.0 eq), compound 10 (817 g, 4.51 mol. 1.03 eq), and N-hydroxybenzotriazole (651 g, 4.82 mol, 1.1 eq) in 14.0 L (dichloromethane) is treated with NMM (N-methyl morpholine) (885 g, 8.76 moll, 2.0 eq), followed by a portion wise addition of N-(3-dimethyaminopropyl)-N'-ethylcarbodiimide hydrochloride (923 g, 4.82 mol 1.10 eq). The reaction is at 20° C. and the reaction progress is monitored by in-process HPLC. After the reaction is completed, the reaction mixture is processed by standard extraction procedures to afford compound 11 (2192 g, 9.1% yield). An HPLC analysis is expected to show the purity of compound 11 to be about 97-98%. A chiral HPLC method is expected to show that the enantiomeric purity of compound 11 is maintained (from compound 9) during Step 1. No undesired enantiomer is expected to be detected.

Step 2A: Preparation of Compound 13

A mixture of compound 1-3 (1250 g, 2.30 mol), THF (13.8 L), and methanol 9.4 L) is cooled to 10° C. and treated dropwise over 30 minutes with 4 molar equivalents of lithium hydroxide delivered as a 5% solution in water. The reaction mixture is warmed up to room temperature with stirring and the progress is monitored by in-process HPLC. After the reaction is completed, the pH of the reaction mixture is neutralized with aqueous HCl, partially concentrated, acidified with aqueous HCl, and extracted with ethyl acetate. Compound 1-4 (1175 g, 96.5% yield) is obtained for which HPLC analysis is expected to show a purity of about 96%. A chiral HPLC method is expected to show that the enantiomeric purity of compound 13 is maintained (from compound 11) during Step 2A. No undesired enantiomer is expected to be detected.

Step 2B: Preparation of Compound 12

A solution of compound 1-3 (2556 g, 4.70 inol) in DC (15.0 L ) is treated with p-toluenesulfonic acid (1073 g, 5.6 mol, 1.2 eq); and the mixture is heated to 40° C. The reaction progress is monitored by in-process HPL. After the reaction is completed, the reaction mixture is cooled to room temperature, treated with an aqueous sodium bicarbonate solution, and then processed by struidard extraction procedures to afford compound 12 (2065 g, 99% yield), the purity of this product is expected to be about 96.4% by HPLC analysis.

Step 3: Preparation of Compound 14

A mixture of compound 12 (1030 g, 2.32 mol, 1.05 eq), HOBt (601 g, 4.45 mol, 2.0 eq), and NNM (670 g, 6.63 mol, 3.0 eq) in chloroform (17.6 L) is treated with a solution of EDAC (511 g, 2.65 mol, 1.2 eq) in chloroform (2.0 L). This mixture is treated by drop wise addition of a solution of compound 13 (1170 g, 2.21 mol, 1.0 eq) and NMM (337 g, 3.33 mol, 1.5 eq) chloroform (4.2 L) and the resultant reaction mixture is stirred at 20-25 °C. The reaction progress is monitored by the in-process HPLC method. After the reaction is completed, the reaction mixture is processed by standard extraction procedures. The solid foam obtained shows excess weight, and a purity of approximately 88% by HPLC analysis. The solid foam obtained is subjected to crystallization from heptanel Compound 14 (1287 g, 61% yield) is obtained and its purity, determined by HPLC analysis, is expected to be about 97.2%.

Step 4: Preparation of Compound 15

A mixture of compound 14 (2516 g, 2.63 mol), THF (16.6 L) and methanol (10.9 L) is cooled to 10° C. and treated drop wise over 45 minutes with 4 equivalents of LiOH delivered as a 5% solution in water, The reaction mixture is wanned up to room temperature with stifling, and the reaction progress is monitored by in-process HPLC. After the reaction is completed, the reaction mixture is neutralized with aqueous HCl, partially concentrated, acidified with aqueous HCl, and extracted with EtOAc. Compound 15 (quantitative yield, 2813 g of the crude product) is obtained and its purity, determined by HPLC analysis, is expected to be about −94.7%. The crude product is directly used in the next step without further purification.

Step 5: Preparation of Compound 16

A solution of compound 15 [1490 g of the crude product prepared in Step 4 above, assumed to be the equivalent of 1297 g (1.38 mol) of pure compound 15] in chloroform (13.0 L) is cooled to 10° C. and treated with ethyl chloroformate (302 g, 2.78 mol, 2.0 eq) in one portion followed by drop wise addition of DIEA (357 g, 2.76 mol, 2.0 eq.) while, monitoring the internal temperature. The reaction mixture is warmed up to ambient temperature with stirring. The reaction progess is monitored to show a complete conversion to the reactive mixed anhydride intermediate by HPLC analysis of a sample that is quenched by 0.5 M ammonia in dioxane and assessed for formation of compound 16 and the consumption of compound 15. After complete conversion of the acid 15 to the anhydride intermediate, the reaction mixture is cooled to 0° C. and treated through a bubbler with ammonia gas (151 g, 8.8 mol 6.4 eq) while monitoring the internal temperature. The reaction progress is monitored by in-process HPLC. After the reaction is completed, the reaction mixture is quenched with water and processed by standard extraction procedures. Compound 16 (quantitative yield, 1322 g of the crude product) is obtained and its purity, determined by HPLC analysis, is expected to be about 93.2%. The crude product is directly used in the next step without further purification.

Step 6: Preparation of Compound 17

A solution of compound 16 (1322 g of the crude product prepared in Step 5 above, assumed to be the equivalent of 1298 g (1.38 mol) of pure compound 16) in DCM (4.4 L) is cooled to 0° C. and treated drop wise with trifluoroacetic acid (2.1 L, 28 mol, 20 eq.) while maintaining the internal temperature to be below about 10° C. The reaction mixture is warmed up to ambient temperature with stirring. The reaction progress is monitored by in-process HPLC. After the reaction is completed, the reaction mixture is rapidly cooled to −20° C. then quenched by addition over 30 minutes to a rapidly stirred −5° C. mixture of NaOH (22 eq.) in water (9.6 L) and DCM (4.5 L). The addition rate is such that the internal temperature of the mixture is maintained at below about 10° C. The quenched reaction mixture is processed by standard extraction procedures to afford compound 17 (1152 g, 99% yield), and its purity, determined by HPLC analysis, is expected to be about 85.0%.

Step 7: Preparation of Compound 18

A mixture of compound 15 (981 g, 1.04 mol, 1.00 eq), compound 17 (894 g, 1.06 mol, 1.02 eq), and HOBt (288 g, 2.1 mol, 2.0 eq) in chloroform (17.9 L) is treated with a solution of EDAC (240 g, 1.25 mol, 1.2 eq) in chloroform (2.2 L) followed by an addition of NMM (161 g, 1.6 mol, 1.5 eq.). The reaction mixture is stirred at 20-25° C. and the reaction progress is monitored by in-process HPLC. After the reaction is completed, the reaction mixture is processed by standard extraction procedures to afford compound 18 (quantitative yield, 1840 g of crude product) as a solid. The purity of the crude product 18 is expected to be determined to be 80.0% by HPLC analysis. The crude product is subjected to a first recrystallization from 2-propanolimethanol followed by second recrystallization from chloroform/ 2-propanol to affbrd a purified compound 18 (1280 g, 69.8% yield), and its purity, determined by HPLC analysis, is expected to be about 95.1%.

Step 8: Preparation of Compound 19

A mixture of DCM (3.1 L), THF (3.1 L), and phosphoric acid (5323 g, 85%, 46.2 mol 65 eq.) is prepared and the purified compound 18 prepared in Step 7 (248 g, 0.707 mol) is added portion wise over 30 minutes. The reaction mixture is stirred at 20-25° C. and the reaction progress is monitored by in-process HPLC. After the reaction is completed, the reaction mixture is quenched with aqueous NaOH (the pH of the reaction mixture is adjusted to 8-9) and processed by standard extraction procedures to afford compound 19 (quantitative yield, 1323 g of crude product). The purity of the crude product is expected to be determined to be about 90.5% by HPLC analysis. The crude product 19 is purified by silica gel chromatography. The purification process uses 30 g of silica gel (230- 400 mesh) per gram of the crude product 19. 1% methanol/DCM to 10% methanol/DCM (in gadient) is used as elution solvents. After the chromatography, of 460 g (39%) of purified compound 19 is obtained. The purity of the purified compound 19, determined by HPLC analysis, is expected to be about 97.5%.

Step 9: Preparation of Delparantag (PMX-60056)

A mixture of the purified compound 19 prepared by Step 8 (417 g 0.251 mol), 10 wt % palladium on carbon (167 g), methanol(16.7 L), and HCl (5.0 eq., in a 7.2 weight % aqueous solution) is subjected to hydrogen gas at 70 psi pressure. The reaction mixture is agitated at 25° C. and the reaction progress is monitored by in-process HPLC. After the reaction is completed, the reaction mixture is filtered and concentrated by co-distillation with acetonitrile to afford a solid product, which is slunied in tert-butylmethyl ether (MTBE), filtered, and dried to afford delparantag, Yield: 300g (91%) (as a penta Hcl), expected HPLC purity about 97.9%

Purification of Delparantag:

Impure delparantag (274 g, 0.209 mol) is dissolved in methanol (13.9 L), and subsequently treated with 28 g of 3-mercaptopropyl ethyl sulfided silica gel and stirred for 90 minutes. The mixture is filtered and concentrated by co-distillation with acetonitrile to afford a solid product, which is slurried in MTBE, filtered, and dried. This purification process is repeated one more time on the purified product obtained previously (266 g, 0.203 mol) and the second purification process results in 219 g of delparantag. Expected HPLC purity: 97.9%, Pd content: 2.7 ppm.

Example 3: PMX-30063 Inhibits PDE4A

Phosphodiesterase type 4 (PDE4) is predominant phosphodiesterase expressed in neutrophils, T cells and macrophages. PDE inhibitors show broad spectrum of anti-inflammatory effects in almost all inflammatory cells. PDE4 inhibitors, block the degadatiye action of PDE4 on cAMP, thereby increasing intracellular levels of cAMP levels which mediate phosphoryiation of protein kinases. PDE4 inhibitors reduce neutrophil chemotaxis, recruitment and activation: inhibit the activation of CD4+ and CD8+ T cells: and inhibit monocytes chemotaxis, Therefore, inhibition of PDEs is expected to have a therapeutic effect in inflammatory diseases such as inflammatory diseases of the gastrointestinal tract. To test if PMX-30063 can inhibit PDE4 phosphodiesterase, inhibition assays of PDE4 were performed, using PMX-30063. The PDE-Glo phosphodiesterase assay was performed according to the Method described for FIG. 1, using 8 ng of PDE4B, 1 µM cAMP substrate and PMX-30063. Data are presented as luminescence units (RLU).

PMX-30063 inhibited PDE4 with an $IC_{50}$ in the 3 µM range (n=5) (FIG. 1). This is the first report of an HDP mimetic inhibiting a PDE. Since in various animal models, inhibition of PDE4 demonstrates pronounced anti-inflammatory effects, inhibition of PDE4 by PMX30063 may have a broad range of anti-intlammatoiy effects on various key effector cells involved in inflammatory diseases of the gastrointestinal tract.

Example 4: PMX-60056 Inhibits PDE4A

Since PMX-30063 inhibited PDE4, it was decided to also assay PMX-60056 for inhibition of PDE4 activity as well. Therefore, phosphodiesterase inhibition assays of PDE4 were performed with PMX-60056.

The PDE-Glo phosphodiesterase assay was perfotmed according to the Method described for FIG. 2, using 8 ng of PDE4B, 1 µM cAMP substrate PMX-60056. Data are presented as luminescence units (RLU).

PMX-60056 inhibited PDE4 with an $IC_{50}$ in the 3 µM range (n=5) (FIG. 2). Since in various animal models PDE4 inhibitions show pronounced anti-inflammatory effects, inhibition of PDE4 by PMX-60056 may have a broad range of anti-inflammatory effects on various key effector cells involved in inflammatory diseases of the gastrointestinal tract.

Example 5: PMX30063 Inhibits PDE3A

Phosphodiesterase is a family of enzymes that catalyze the breakdown of signaling molecule cyclic AMP/or cyclic GMP. cAMP and cGMP are ubiquitous secondary-messenger signaling molecules produced by a large family of cyclases that participate in a multitude of signaling processes. The present inventors hypothesized that HDP may be functioning through the cyclic AMP/cyclic GMP pathways in suppression of proinflammatory response. PDE3 inhibitors block degradation of both cAMP and cGMP which leads to an increase of intracellular cAMP/cGMP concentrations. Therefore, phosphodiesterase inhibition assays of PDE3 were performed with PNLX-30063.

The PDE-Glo phosphodiesterase assay was perfomied according to the Method described for FIG. 3 using 2.75 ng of PDE3A, 1 µM cAMP substrate and PMX-30063. The compounds and PDE3A were mixed and pre-incubated at room temperature for 15 minutes. Substrate was added and the reaction was incubated.

PMX-30063 inhibited PDE3 at an $IC_{50}$ of 1.5 ±0.2 ₁AM (n=4) (FIG. 3). Thus, Ma-30063 acts as both a PDE3 and PDE4 inhibitor as single molecule. Combining the functions of PDE4 and PDE3 inhibition, PMX-30063 can function as an antimicrobial and an anti-inflammatory. Additive and/or synergistic effects are produced when multiple PDEs are inhibited concurrently (Rieder et al. *PLoS One* 2013 2013: 8(2):e56867. doi: 10.13714journal.pone.0056867. Epub 2013 Feb. 28), This is expected to reduce inflammation, as occurs in inflammatory diseases of the gastrointestinal tract.

Example 6: PMX-60056 Inhibits PDE3A

Since PMX-30063 inhibited PDE3, it was decided to also assay PMX-60056 for inhibition of PDE3 activity as well. Therefore, phosphodiesterase inhibition assays of PDE3 were performed with BMX-60056. The PDE-Glo phosphodiesterase assay was performed according to the Method described for FIG. 4 using 2.75 ng of PDE3A, 1 µM cAMP substrate and PMX-60056. The compounds and PDE3A were mixed and pre-incubated at room temperature for 15 minutes. Substrate was added and the reaction was incubated.

PMX-60056 inhibited PDE3 at an $IC_{50}$ of 3 µM (FIG. 4). Thus, PMX-60056 acts as both a PDE3 and PDE4 inhibitor as single molecule. Combining the functions of PDE4 and PDE3 inhibition, PMX-60056 can function as an antimicrobial and an anti-inflammatory. Additive and/or synergistic effects are produced when multiple PDEs are inhibited concurrently. This is expected to reduce inflammation as occurs in inflammatory diseases of the gastrointestinal tract.

Example 7: PMX-30063 Inhibits TNF-α

The intestinal lamina propria contains a complex population of immune cells that balance the requirement for immune tolerance of luminal microhiota with the need to defend against the pathogen, excessive entry of luminal microbiota, or both. The hallmark of active inflammatory bowel disease is a pronounced infiltration into the lamina propria of innate immune cells (neutrophils, macrophages, dendritic cells, and natural killer T cells) and adaptive immune cells ('U cells and B cells), Increased numbers and activation of these cells in the intestinal mucosa elevate local levels of TNF-α, interleukin-1β, interleukin-6 (IL-6), interferon-gamma (IFN-γ), and cytokines of the interleukin-23-Th17 pathway.

The proinflammetery cytokine TNF-alpha has been identified as playing a pivotal role in the inflammatory cascade that causes chronic intestinal inflammation in inflammatow diseases of the gastrointestinal tract. TNT-α is a key mediator of neutrophilic inflammation in inflammatory diseases of the gastrointestinal tract. Anti-TNF-alpha antibody has been Shown to mitigate this inflammatory process. TNF-alpha inhibitors have been shown to induce apoptosis of TNF alpha producing immune cells, reducing the production of a variety of downstream proinflammatoty cytokines from these and other cells. Hence its inhibition has potential to target multiple components of inflammatory diseases of the gastrointestinal tract. Therefore, the TNIF-α inhibition assay was performed with PMX-30063.

The TNT-α inhibition assay was performed according to the Method described for FIG. 5 NR8383 rat macrophage cells were pretreated with PMX-30063 for 45 minutes followed by treatment with 1 μg/ml LPS for 8 hours. TNF-α concentrations in the supernatants were determined by ELEA using an immunoassay kit specific for rat TNF-α (R&D Systems).

PMX-30063 inhibited the LPS induced TNF-α production in NR8383 rat macrophages (CRL-2192, ATCC) by about 50% at 0.5 μM PMX-30063 (FIG. 5). As an anti-inflammatory HDP, PMX-30063 reduces the levels of TNF alpha, which may be very elective for treatment of inflanmiatory diseases of the gastrointestinal tract.

Example 8: PMX-6005 Inhibits TNF-α

Since PMX-30063 inhibited TNF-α, it was decided to also assay PMX-60056 for inhibition of TNF-α activity as well. The INF-α inhibition assay was performed according to the Method described for FIG. 6. NR8383 rat macrophage cells (CRL-2192. ATCC) were pretreated with PMX-60056 for 45 minutes followed by treatment with 1 μg/ml LPS for 8 hours. INF-α concentrations in the supernatants were determined by ELISA using an immunoassay kit specific ICr rat INF-α (R&D Systems).

PMX-60056 inhibited the ITS induced TNF-α production in NR8383 rat macrophages by more than 50% at 62.5 nM PMX-60056 (FIG. 6). As an anti-inflammatoty HDP,PMX-60056 reduces the levels of TMFalpha, an activity which may be very effective for treatment of inflammatory diseases of the gastrointestinal tract.

Example 9: PMX-30063 Inhibits Mionocyte Chemoattrac ant Protein-1

MCP-1 is produced by a variety of cells including dendritic cells, macrophages, endothelial cells and fibroblasts, and its expression is upregulated after exposure to inflammatory stimuli such as IL-1 and TNF-alpha. MCP-1 was originally identified as monocyte-specific chemoattractant but was later on shown to act on T cells, mast cells, basophils, and natural killer cells. Elevation of MCP-1 is observed in mucosal tissue from patients with Crohn's disease and ulcerative colitis and also in experimental models of colitis. Since MCP-1 binds to C-C Chemokine Receptor type 2 (CCR2),and MCP-1 can induce T cell and monocytic migration, this chemokine contributes to recruitment of these cells in inflammatory diseases of the gastrointestinal tract and plays an important role in the induction of the in response. Therefore, the MCP-1 inhibition assay was performed with PMX-30063.

The MCP-1 inhibition assay was performed according to the Method described for FIG. 7. When NR8383 rat macrophage cells CRL-2192, ATCC) were pretreated with PMX-30063 for 45 minutes, we observed a strong inhibition of MCP-1 induction after LPS (1 μg/ml) stimulation for 8 hours (FIG. 7).

A minimum of 25% decrease in MCP-1 levels at 0.5 μM for PMX-30063 was observed. These results further demonstrate the potent anti-inflammatory effects of PMX-30063.

Example 10: PMX-60056 Inhibits Monocyte Chemoattractant Protein-1

Since PMX-30063 inhibited MCP-1, it was decided to assay PMX-60056 for inhibition of MCP-1 activity as well. The MCP-1 inhibition assay was performed according to the Method described for FIG. 8. When NR8383 rat macrophage cells (CRL-2192ATCC) were pretreated with PMX-60056 for 45 minutes, we observed a strong inhibition of MCP-1 induction after LPS (1 μg/ml) stimulation for 8 hours (FIG. 8).

A minimum of 25% decrease in MCP-1 levels at 0.5 μM for PMX-60056 was observed. These results further demonstrate the potent anti-inflammatory effects of PMX-60056.

Example 11: PMX-30063 Inhibits Matrix-Metalloproteinase-9

Matrix metalloproteinase (MMP-9) has been shown to be involved in the pathogenesis of inflammatory diseases such as inflammatory diseases of the gastrointestinal tract. Inappropriate expression and excessive activity of MMPs has been implicated in the tissue destructive processes associated with inflammatory diseases of the gastrointestinal tract. Chronic inflammation is orchestrated by inflammatory cells which release proinflammatory and destructive mediators such as elastases, proteases, interleukin-8 (IL-8), leukotriene B-4 (LTB4), TNF alpha, and MMPs that attract more inflammatory cells [Gueders, M. M, Foidart, M., Noel, A. & Cataldo, D.D. Matrix metalloproteinases (MMPs), and tissue inhibitors of MMPs in the respiratory tract: potential implications in asthma and other lung diseases. *European Journal of Pharmacology* 533, 133-144, (2006); Hurst, J, R. & Wedzicha, J. A. The biology of a chronic obstructive puhnonary disease exacerbation. *Clinics in chest medicine* 28, 525-536, (2007)]. These proinflammatory cytokines lead to prolonged cycles of chronic inflammation. Therefore, the MMP-9 inhibition assay was perfbmied with PMX-30063.

The MMP-9 inhibition assay was performed according to the Method described lbr FIG. 9. Levels of MMP-9 activity from supernatants of NR8383 rat macrophages CRL-2192, ATCC) pretreated with PN-30063 for 45 minutes thllowed by LPS (1 μg/ml) induction for 8 hours were determined.

A 50% decrease in MMP-9 levels at a 12.5 μM concentration of PMX-30063 was observed (FIG. 9), These results fuither demonstrate the potent anti-inflannuatory effects of PMX-30063.

Example 12: PMX-30063 Inhibits IL-6 Induction

The intestinal lamina propria contains a complex population of immune cells that balance the requirement for inmune tolerance of luminal microbiota with the need to defend against the pathogen, excessive entry of luminal microbiota, or both. The hallmark of active inflammatory bowel disease is a pronounced infiltration into the lamina propria of innate immune cells (neutrophils, macrophages, dendritic cells, and natural killer T cells) and adaptive immune cells (T cells and B cells). Increased numbers and activation of innate immune cells (neutrophils, macrophages, dendritic cells, and natural killer T cells) and adaptive immune cells (T cells and B cells). Increased numbers and activation of these cells in the intestinal mucosa elevate local levels of TNF-α, interleukin-β, interleukin-6 (IL-6), interferon-gamma (IFN-γ), and cytokines of the interleukin-23-Th17 pathway.

Influencing the production of IL-6 can change the balance of effector CD4+ T cell subsets and induce B cell antibody production. Moreover, given that IL-6 is mostly produced from innate cells such as macrophages, neutrophils and mast cells, it is a strategic bridge between the innate and the adaptive system. IL-6 has been shown to be key player in chronic inflammation. Levels of circulating IL-6 are elevated in several inflammatory diseases including Crohn's disease. Expression of 1L-6 is enhanced at the site of inflammation and blockade of IL-6 and IL-6 signaling is effective at prevention and treatment in models of inflammatory disease like inflammatory diseases of the gastrointestinal tract. Therefore, the inhibition of IL-6 induction assay was performed with PMX-30063.

The inhibition of IL-6 induction assay was peraumed according to the Method described for FIG. 10. Pretreatment for 8 hours with PMX-30063 inhibited the LPS (1 µg/ml) induced IL-6 production in NR8383 rat macrophages (CRL-2192ATCC) by about 50% at 0.5 µM of PMX-30063 (FIG. 10), an activity which may be very effective for treatment of inflammatory diseases of the gastrointestinal tract.

Summary of Anti-Inflammatory Activity for PMX-30063 and PMX-60056 (FIGS. 1-10)

As an anti-inflammatory agent, PMX-30063 reduced the levels of TNF-α, MCP-1, MMP-9, and IL-6. PMX-60056 also reduced the levels of TNIF-α, and MCP-1. The anti-inflammatory functions of PMX-30063 and PNLX-60056 may be mediated by reducing several proinflammatory pathways and regulating the intracellular concentration of cyclic nucleotide and its signaling pathways consequently effecting a myriad of biological responses in chronic inflammatory diseases such as infla mmatory diseases of the gastrointestinal tract.

In Vivo Distribution Study Demonstrates PMX30063 Given Orally Remains Primarily in the Small Intestine Example 13: Concentration of PMX-30063 in the Plasma Following Intravenous or Oral Administration to Mice To evaluate the extent of distribution into the plasma following administration of PMX-30063, a study was conducted to measure PMX-30063 plasma concentrations following 10 mg/kg given PO or 5 mg/kg given IV in male Balb/c mice (Study 16009-12001) according to the Method described for FIG. 11.

The plasma concentration versus time curves for PMX-30063 following IV or PO administration is shown (FIG. 11). The peak concentration of PMX-30063 given IV was 4.8, 415±7803 ng/mL, whereas when given PO, peak concentration in plasma was 33.7±8.56 ng/mL. This demonstrates that less than 0.1% of PMX-30063 that is administered orally enters the circulation which greatly reduces the risk of systemic toxicity.

Example 14: Concentration of PMX-30063 in the Small Intestine Following Oral Administration to Mice The concentration of PMX-30063 in small intestine following PO administration of 10 mg/kg was conducted according the Method described for FIG. 12. At 1 hour, the concentration in the small intestine peaked at 38,941±4703 ng/gam of tissue (FIG. 12). This demonstrates that PMX-30063 when given orally enters into the small intestine tissues where it can exert its anti-inflammatory effects at the local level.

Example 15: Ratio of Intestine to Plasma Concentration Following Oral Administration of PMX-30063

The intestine to plasma concentration ratio following oral administration of PMX-30063 was calculated based on data derived from FIGS. 11 and 12 according to the Method described for FIG. 13.

In the first hour, these ratios ranged from 2243 to 4323 demonstrating that less than 0.1% of PMX-30063 initially enters the circulation following oral administration. Over 4 hours., still less than 0.5% enters the circulation following oral administration (FIG. 13).

Pharmacokinetics parameters of PMX-30063 in the plasma and small intestine of male mice following intravenous and oral administration of PMX-30063 are shown in the Table below. These data also demonstrate that total exposure (AUC) its the blood is less than 0.5% upon oral administration,

| Plasma: | AUC(0-t) ng/mL*h | AUC(0-∞) ng/mL*h | MRT(0-∞) H | t½ h | Tmax h | Vz L/kg | CL L/h/kg | Cmax ng/mL | F* % |
|---|---|---|---|---|---|---|---|---|---|
| IV (5 mg/kg) | 97668 | 97818 | 2.86 | 2.76 | 0.0830 | 0.204 | 0.0511 | 48415 | |
| PO (10 mg/kg) | 111 | 113 | 2.68 | 1.26 | 2.00 | NA | NA | 33.7 | 0.0579 |

| Intestine: | AUC(0-t) ng/g*h | AUC(0-∞) ng/g*h | MRT(0-∞) H | t½ h | Tmax h | Vz L/kg | CL L/h/kg | Cmax ng/g |
|---|---|---|---|---|---|---|---|---|
| PO (10 mg/kg) | 86089 | 89525 | 1.52 | 0.790 | 1.00 | NA | NA | 38941 |

FIG. 11, FIG. 12, FIG. 13 and the Table demonstrate that with oral administration, PMX30063 is taken up by the tissues in the small intestine but <0.5% enters the circulation which offers a great advantage for treatment of intestinal epithelium with low risk of systemic toxicity.

Example 16: Effect of PMX-30063 on Intestine Weights In Vivo in an Ulcerative Colitis Model PMX-30063 was evaluated fix in vivo efficacy in an ulcerative colitis (UC) model according to the Method described for FIG. 14. Briefly, UC was induced by injecting 4% acetic acid into the rectum. Four days later, animals were treated once daily for 5 days with PMX-30063 at either 100 mg/kg, 200 mg/kg or 400 mg/kg intrarectally, or with 5-ASA, or no treatment.

Intestine weights were significantly reduced by 17% at the 400 mg/kg dose compared to untreated controls (p=0.02) (FIG. 14, Table below). Since UC causes inflammation of tissues, it was expected that the intestine weights would decrease upon treatment with PMX-30063.

Example 17 PMX-30063 Demonstrated In Vivo Efficacy in an Ulcerative Colitis Model PMX-30063 was evaluated for efficacy in an ulcerative colitis (UC) model according to the Method described for FIG. 15.

A dose dependent decrease in ulcerative colitis scare in animals was observed (FIG. 15). Treatment with PMX-30063 at 100 mg/kg reduced the median LTC score by 33% and at 200 and 400 mg/kg further reduced the TJC score by 67%, but not significantly (Table below). in annuals treated with 5-ASA, the UC score was also reduced by 67%, but not significantly. Maximum weight loss was 12% among all goups.

|  | Student's t test Day 7 p value | |
| --- | --- | --- |
|  | intestine weight | ulcerative colitis score |
| 100 mg/kg vs. untreated | 0.29 | 0.97 |
| 200 mg/kg vs. untreated | 0.34 | 0.21 |
| 400 mg/kg vs. untreated | 0.02 | 0.08 |
| 100 mg/kg vs. 5-ASA | 0.11 | 0.27 |
| 200 mg/kg vs. 5-ASA | 0.14 | 0.95 |
| 400 mg/kg vs. 5-ASA | 0.54 | 0.35 |

Therefare, this preliminary study suggested that PMX-30063 given intrarectally may be effective in reducing the clinical symptoms of ulcerative colitis while being well-tolerated. We hypothesize that PMX-30063, as an HDP mimetic may be functioning through the cyclic AMP/cyclic GMP pathways in suppression of proinflammatory response, PDE4 is a predominant phosphodiesterase expressed in neutrophils, T cells and macrophages and PDE4- inhibitors reduce neutrophil chemotaxis, recruitment and activation, inhibits the activation of CD4+ and CD8+ T cells, and inhibits monocytes chemotaxis. Hence, PDE4 has a broad range of anti-inflammatory effects on various key elector cells that may be involved in ulcerative colitis. Crohn's disease and other inflammatory bowel diseases.

Summary of Biological Data

In summary, demonstrating anti-inflammatory activity, PMX-30063 (brilacidin) reduced the levels of TNF-α, MCP-1, MMP-9, and IL-6. PMX-60055 (delparantag) also reduced the levels of TNF-α, and MCP-1. The anti-inflammatory functions of PMX-30063 and PMMA 60056 may be mediated by reducing several proinfluarnakny pathways and regulating the intracellular concentration of cyclic nucleotide and its signaling pathways consequently effecting a myriad of biological responses in chronic inflammatory diseases such as inflamnaatoiy diseases of the gastrointestinal tract.

PMX-30063 has both antimicrobial and anti-inflammatory effects so it can be used when both infection and inflammation are present. It can also be used to treat inflammation when there is no infection. PMX-60056 may be used together with PMX-30063 or with another antibiotic when both inf&tion and inflammation are present. PMX-30063 andior PMX-60056 may be used when infection is absent but inflammation is present or to provide prophylaxis against inflammation. The use of PMX-30063 and/or PMX-60056 for infections that may result in inflammation would provide prophylaxis that could prevent inflammation and thus break a potential vicious cycle between chronic bacterial colonization, inflammation, and epithelial damage. PMX-30063 and PNLX-60056 have the potential to prevent the induction and progression of inflammatory diseases of the gastrointestinal tract, unlike current therapies which have limited efficacy in inhibiting chronic inflammation, do not reverse the pathology of disease, and fail to modify the factors that initiate and drive the long-term progression of disease.

Example 18: Proposed Clinical Study

A Phase 2 Open Label, Multicenter Study to Assess the Efficacy and Safety of Rectally Administered Brilacidin (PMX-30063) for Induction of Remission in Subjects With Active Mild to Moderate Ulcerative Proctitis (UP) or Ulcerative Proctosigmoiditis (UPS).

At time of screening for enrollment, subjects who meet endoscopic enrollment criteria will have two (2) rectal and two (2) sigmoid biopsies obtained for possible future use in analysis of efficacy results (biopsy results are not required for enrollment). All subjects will receive brilacidin administered per rectum. Assignment to treatment groups will be sequential at each participating site. No randomization will be performed. At any one site, no more than 50% of enrolled subjects may have UPS.

PMX-30063 (brilacidin) will be administered rectally, in water for injection (WFI) as a retention enema, at a dose of A) 25 mg in 60 mL once daily at bedtime B) 50 mg in 60 mL once daily at bedtime, C) 2.5 mg in 60 mL twice daily morning and at bedtime, Or D) 50 mg in 60 mL twice daily morning and at bedtime for 6 weeks. As a proof of concept study, approximately 10 subjects for each arm will be enrolled into the study. During the study, eligible subjects will be allowed to maintain previously established oral 5-ASA treatment at doses up to 4.8 grams per day. Periodic safety monitoring, including physical examinations, vital signs, laboratory testing, and recording of AEs and concomitant medications, will be performed during the study.

The primary objective is to assess the frequency of clinical and endoscopic remission after 6 weeks of treatment with PMX-30063 administered per rectum in subjects with active UP or UPS based on the Modified Mayo Disease Activity Index (MMDAI) score. The primary efficacy measure is the percentage of patients achieving remission, dermed as an endoscopy score >1, rectal bleeding score=0, and improvement or no change from baseline in stool frequency subscales of the MMDAI at week 6.

Secondary objectives are to evaluate the safety of brilacidin when administered per rectum .and to estimate the statistical power for subsequent trial(s) in this indication. Key secondary outcomes include:

Percentage of subjects with clinical response

Percentage of subjects achieving a rectal bleeding MMDAI subscale score of 0

Percentage of subjects with an endoscopy MMDAI subscale score <1 at week 6

Change in fecal calprotectin

Change in serum C-reactive protein (CRP)

Change in serum IL-6

Improvement in health related Quality of life (QOL)

Pharmacokinetics data

I claim:

1. A method of treatment of ulcerative proctitis and ulcerative proctosigmoiditis in a mammal in need thereof, said method comprising administering to the mammal a therapeutically effective amount of brilacidin or a pharmaceutically acceptable salt thereof.

2. A method according to claim 1, wherein brilacidin or a pharmaceutically acceptable salt thereof is administered together with an antibiotic.

3. A method as claimed in claim 1 wherein said therapeutically effective amount of brilacidin is a dose of between 50 mg to 200 mg per day.

4. The method according to claim 1 wherein said brilacidin or said pharmaceutically acceptable salt thereof is administered in a rectal enema.

5. A method of treatment of ulcerative colitis, in a mammal comprising administering to the mammal in need of such treatment a therapeutically effective amount of brilacidin or a pharmaceutically acceptable salt thereof.

6. A method according to claim 5, wherein brilacidin or a pharmaceutically acceptable salt thereof is administered together with an antibiotic.

7. The method according to claim 5 wherein said compound is administered orally.

8. A method according to claim 7 wherein said compound is administered at a daily dose of 0.01 to 70 milligrams per kilogram of body weight of the patient.

9. A method according to claim 7 wherein said compound is administered at a daily dose of 0.5 to 20 milligrams per kilogram of body weight of the patient.

* * * * *